United States Patent
Jang et al.

(10) Patent No.: US 12,319,695 B2
(45) Date of Patent: Jun. 3, 2025

(54) SULFONAMIDE DERIVATIVE WITH FUSED PYRIMIDINE SKELETON, HAVING EPIDERMAL GROWTH FACTOR RECEPTOR MUTATION INHIBITORY EFFECT

(71) Applicant: HANMI PHARM. CO., LTD., Hwaseong-si (KR)

(72) Inventors: Sun Young Jang, Hwaseong-si (KR); Mi Ra Kim, Hwaseong-si (KR); Ji Young Jeon, Hwaseong-si (KR); Eun Joo Kwak, Hwaseong-si (KR); Sun Hoe Lee, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 1009 days.

(21) Appl. No.: 17/278,017

(22) PCT Filed: Sep. 20, 2019

(86) PCT No.: PCT/KR2019/012207
§ 371 (c)(1),
(2) Date: Mar. 19, 2021

(87) PCT Pub. No.: WO2020/060268
PCT Pub. Date: Mar. 26, 2020

(65) Prior Publication Data
US 2021/0380589 A1 Dec. 9, 2021

(30) Foreign Application Priority Data

Sep. 20, 2018 (KR) ......................... 10-2018-0113083
Aug. 13, 2019 (KR) ......................... 10-2019-0098931

(51) Int. Cl.
*C07D 487/04* (2006.01)
*A61P 35/00* (2006.01)
*C07D 519/00* (2006.01)

(52) U.S. Cl.
CPC ............ *C07D 487/04* (2013.01); *A61P 35/00* (2018.01); *C07D 519/00* (2013.01)

(58) Field of Classification Search
CPC ...... C07D 487/04; C07D 519/00; A61P 35/00
See application file for complete search history.

(56) References Cited

U.S. PATENT DOCUMENTS

| 9,428,508 | B2 | 8/2016 | Xiao et al. |
| 10,508,118 | B2 | 12/2019 | Deng et al. |
| 2013/0079324 | A1 | 3/2013 | Cheng et al. |
| 2013/0281438 | A1 | 10/2013 | Xiao et al. |
| 2014/0296216 | A1 | 10/2014 | Ding et al. |

FOREIGN PATENT DOCUMENTS

| CN | 105884695 A | 8/2016 | |
| EP | 3 290 420 A1 | 3/2018 | |
| KR | 10-2016-0007677 A | 1/2016 | |
| KR | 10-2017-0141783 A | 12/2017 | |
| KR | 10-2019-0067699 A | 6/2019 | |
| WO | 2017/066428 A1 | 4/2017 | |
| WO | WO-2018098561 A1 * | 6/2018 | ........... A61K 31/498 |
| WO | 2019/067699 A1 | 4/2019 | |
| WO | WO-2019112344 A1 * | 6/2019 | ........... A61K 31/506 |

OTHER PUBLICATIONS

Han European Journal of Medicinal Chemistry 124 (2016) 583e607 (Year: 2016).*
Choe et al. Bullof the Korean Chem Soc. 2017. 38. 1353-1357 (Year: 2017).*
Clin Cancer Res (2007) 13 (10): 2890-2896. (Year: 2007).*
Hyeonjeong Choe, et al., "Structure-Activity Relationship Study of 2,4-Dianilinopyrimidine Containing Methanesulfonamide (TRE-069) as Potent and Selective Epidermal Growth Factor Receptor T790M/C797S Mutant Inhibitor for Anticancer Treatment#", Bulletin of the Korean Chemical Society, Oct. 13, 2017, pp. 1353-1357, vol. 38.
Chee-Seng Tan, et al., "Third generation EGFR TKIs: current data and future directions", Molecular Cancer, Feb. 19, 2018, pp. 1-14, vol. 17, No. 29.
Shuhang Wang, et al., "EGFR C797S mutation mediates resistance to third-generation inhibitors in T790M-positive non-small cell lung cancer", Journal of Hematology & Oncology, Jul. 22, 2016, pp. 1-5, vol. 9, No. 59.
Kenneth S. Thress, et al., "Acquired EGFR C797S mediates resistance to AZD9291 in advanced non-small cell lung cancer harboring EGFR T790M", Nat Med., Jun. 2015, pp. 1-11, vol. 21, No. 6.
Martin L. Sos, et al., "Chemogenomic Profiling Provides Insights into the Limited Activity of Irreversible EGFR Inhibitors in Tumor Cells Expressing the T790M EGFR Resistance Mutation", Cancer Research, Feb. 1, 2010, pp. 868-874, vol. 70, No. 3.
Anja Michalczyk, et al., "Structural insights into how irreversible inhibitors can overcome drug resistance in EGFR", Bioorganic & Medicinal Chemistry, Feb. 20, 2008, pp. 3482-3488, vol. 16.
Danan Li, et al., "Bronchial and Peripheral Murine Lung Carcinomas Induced by T790M-L858R Mutant EGFR Respond to HKI-272 and Rapamycin Combination Therapy", Cancer Cell, Jul. 2007, pp. 81-93, vol. 12.

(Continued)

*Primary Examiner* — Clinton A Brooks
*Assistant Examiner* — Jerica Katlynn Wilson
(74) *Attorney, Agent, or Firm* — Sughrue Mion, PLLC

(57) ABSTRACT

A novel fused pyrimidine based sulfonamide derivative represented by Formula I, a solvate thereof, or a pharmaceutically acceptable salt thereof, and a pharmaceutical composition including the same as an active ingredient are disclosed. The novel fused pyrimidine based sulfonamide derivative can effectively suppress the growth of cancer cells and resistance to drugs, which are induced by mutations in the tyrosine kinase domain of epidermal growth factor receptors, or the growth of cancer cells having such resistance.

3 Claims, No Drawings

(56) References Cited

OTHER PUBLICATIONS

Helena A. Yu, et al., "Analysis of Tumor Specimens at the Time of Acquired Resistance to EGFR-TKI Therapy in 155 Patients with EGFR-Mutant Lung Cancers", Clinical Cancer Research, Apr. 15, 2013, pp. 2240-2247, vol. 19, No. 8.

Nancy E. Hynes, et al., "ERBB Receptors and Cancer: The Complexity of Targeted Inhibitors", Nature Reviews Cancer, May 2005, pp. 341-354, vol. 5.

Alan Wells, "Molecules in focus EGF receptor", The International Journal of Biochemistry & Cell Biology, 1999, pp. 637-643, vol. 31.

Ramesh Butti, et al., "Receptor tyrosine kinases (RTKs) in breast cancer: signaling, therapeutic implications and challenges", Molecular Cancer, Feb. 19, 2018, pp. 1-18, vol. 17, No. 34.

International Searching Authority, International Search Report for PCT/KR2019/012207 dated Dec. 30, 2019 (PCT/ISA/210).

Extended European Search Report dated Apr. 11, 2022 in Application No. 19862042.9.

\* cited by examiner

SULFONAMIDE DERIVATIVE WITH FUSED PYRIMIDINE SKELETON, HAVING EPIDERMAL GROWTH FACTOR RECEPTOR MUTATION INHIBITORY EFFECT

CROSS REFERENCE TO RELATED APPLICATIONS

This application is a National Stage of International Application No. PCT/KR2019/012207 filed Sep. 20, 2019, claiming priorities based on Korean Patent Application No. 10-2018-0113083 filed Sep. 20, 2018 and Korean Patent Application No.
10-2019-0098931 filed Aug. 13, 2019.

TECHNICAL FIELD

The present invention relates to a novel fused pyrimidine based sulfonamide derivative having inhibiting efficacy against a mutant epidermal growth factor receptor, and a pharmaceutical composition comprising the same as an active ingredient.

BACKGROUND ART

Epidermal growth factor receptor (EGFR) is a protein composed of a receptor portion and a tyrosine kinase portion, and has a role to transmit extracellular signals into cells by passing through the cell membrane. EGFR plays an essential role in normal cellular regulation through intracellular signal transduction, but EGFR overexpression or activating EGFR mutations characterized by ligand-independent tyrosine kinase activity are also unable to regulate signals, and this is known to induce growth, differentiation, neovascularization, metastasis, and resistance expression of cancer cells by activating the cellular signaling system (Wells A. Int J Biochem Cell Biol., 1999, 31, 637 and Nancy E. Hynes and Heidi A. Lane, *Nature Reviews Cancer* 5, 341, 2005). It has been reported that EGFR is abnormally overexpressed or mutations are frequent in most solid cancer cells, which is associated with a poor prognosis. Among them, activating EGFR mutations such as the L858R point mutation of exon 21 or the in-frame deletion of exon 19 of the EGFR tyrosine kinase domain are known to be important causes of non-small cell lung cancer. Therefore, under the prediction that the anticancer effect will be excellent if signal transduction of cancer cells through the epithelial growth factor receptor is blocked, research to develop anticancer agents targeting the epithelial growth factor receptor is actively underway.

Among small molecule substances, the first drug developed as an EGFR tyrosine kinase inhibitor is Gefitinib, a reversible inhibitor that selectively inhibits EGFR (Erb-B1) as an EGFR subtype. Another drug with such characteristics is Erlotinib. Such EGFR-targeting therapeutic agents are mainly used in patients with EGFR activating mutations with non-small cell lung cancer (NSCLC) as a main indication.

However, it has been reported that patients with non-small cell lung cancer with EGFR activating mutations administered with gefitinib or erlotinib became resistant to the drug after about 8 to 16 months, and about 60% of them showed resistance due to the EGFR T790M mutation (Helena A. Yu et al., Clin Cancer Res. 19(8), 2240, 2013).

In order to overcome the resistance to existing EGFR inhibitors such as gefitinib or erlotinib, a quinazoline based irreversible inhibitor has been proposed (Danan Li et al., Cancer Cell 12, 81, 2007; and Anja Michalczyk et al., Bioorganic & Medicinal Chemistry 16, 3482, 2008). However, EGFR irreversible inhibitors also have high activity against EGFR WT (wild-type), which is also present in normal cells. Therefore, when a dosage to overcome resistance caused by the EGFR T790M mutation is administered, it causes serious side effects. Consequently, it has limitations in clinical application. (Martin L. Sos, et al., Cancer Res. 70, 868, 2010).

As an alternative to this, as third-generation EGFR inhibitors, which are EGFR mutation-selective inhibitors, osimertinib, olmutinib, naquotinib, avitinib, and multiple other drugs have been under clinical development. Among them, osimertinib has been used as a therapeutic agent for non-small cell lung cancer patients with EGFR activating mutations such as L858R point mutations or in-frame deletions of exon 19, and EGFR T790M mutations. However, it is known that non-small cell lung cancer patients with EGFR T790M mutations administered with osimertinib become resistant to drugs after about 10 months due to activation of other resistance mechanisms, of which C797S mutations are known to appear in a high proportion of 20% or more (Thress, K. S. et al. *Nat. Med.* 21,560, 2015; Shuhang Wang et al. *Journal of Hematology* & Oncology, 9, 59, 2016 and Tan et al. *Molecular Cancer,* 17, 29, 2018). The C797S mutation is a point mutation in which cysteine 773 (Cys773), which forms a covalent bond with irreversible EGFR inhibitors, is changed to serine, and does not form covalent bonds with irreversible EGFR inhibitors, causing a reduction in drug reactivity.

As described above, the development of EGFR-targeted therapeutic agents shows limitations in that the drug efficacy cannot be maintained for more than a certain period of time due to primary and secondary resistance expression. In particular, studies on EGFR C797S mutation are desperately required for effective therapies, as there are no substances under clinical studies other than reports of early stage preclinical studies.

DESCRIPTION OF EMBODIMENTS

Technical Problem

An objective of the present invention is to provide a novel compound with fewer side effects while selectively and effectively inhibiting the growth of cancer cells and resistance to drugs, which are caused by mutations in the tyrosine kinase domain of epidermal growth factor receptors (EGFR), or cancers having such resistance.

Another objective of the present invention is to provide a pharmaceutical composition for inhibiting cancer cell growth, containing the above-described compound as an active ingredient.

Solution to Problem

According to an aspect of the present invention, provided are compounds represented by Formula (I), solvates or stereoisomers thereof, or pharmaceutically acceptable salts thereof.

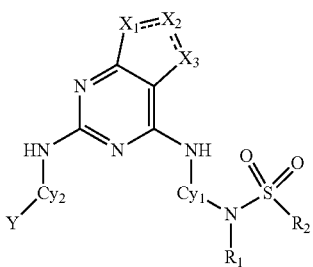

Another aspect of the present invention, provided is a pharmaceutical composition for the prevention or treatment of a cancer having EGFR mutation, the composition including a pyrimidine derivative of Formula I, a solvate thereof, a stereoisomer thereof, or a pharmaceutically acceptable salt thereof, and a pharmaceutically acceptable carrier.

Advantageous Effects of Disclosure

According to an aspect of the present invention, compounds of Formula I, solvates or stereoisomers thereof, or pharmaceutically acceptable salts thereof can selectively and effectively suppress the growth of cancer cells and resistance to drugs, which are caused by mutations in the tyrosin kinase domain of epidermal growth factor receptors (EGFR), or cancers having such resistance.

MODE OF DISCLOSURE

Hereinafter, the present invention will be described in greater detail.

All the technical terms used herein are used with the same meaning as understood by a person skilled in the art, unless defined otherwise. In addition, although preferred methods or samples are described herein, those similar or equivalent thereto are included in the scope of the present invention. In addition, the numerical values described herein are considered to include the meaning of "about" even if not specified. The contents of all publications referred to herein are incorporated herein by reference in their entirety.

One aspect provides a compound represented by Formula I, or a solvate or pharmaceutically acceptable salt thereof:

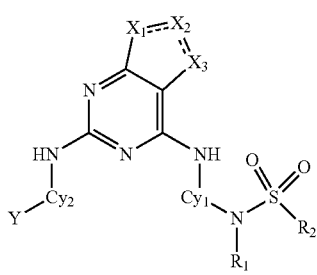

[Formula I]

wherein in Formula I, $R_1$ and $R_2$ are each independently selected from among a substituted or unsubstituted $C_1$-$C_6$ alkyl group, a substituted or unsubstituted $C_3$-$C_{10}$ cycloalkyl group, or a substituted or unsubstituted amine group;

$Cy_1$ is a $C_3$-$C_{12}$ aryl or $C_1$-$C_{12}$ heteroaryl, wherein the aryl or heteroaryl may have one or more substituents selected from the group consisting of halogen, a cyano group, a hydroxyl group, a thiol group, a nitro group, a substituted or unsubstituted $C_1$-$C_6$ alkyl group, a substituted or unsubstituted $C_3$-$C_{10}$ cycloalkyl group, a substituted or unsubstituted $C_1$-$C_{10}$ heterocycloalkyl group, a substituted or unsubstituted $C_1$-$C_6$ alkoxy group, —O(CH$_2$)$_a$-(Q$_1$), and a $C_1$-$C_6$ alkoxy group substituted with one or more halogens;

$Cy_2$ is a $C_3$-$C_{12}$ aryl or $C_1$-$C_{12}$ heteroaryl, wherein the aryl or heteroaryl may have one or more substituents selected from the group consisting of halogen, a cyano group, a hydroxyl group, a thiol group, a nitro group, a substituted or unsubstituted $C_1$-$C_6$ alkyl group, a substituted or unsubstituted $C_3$-$C_{10}$ cycloalkyl group, and a substituted or unsubstituted heterocycloalkyl group;

Qi is selected from the group consisting of hydrogen, a hydroxyl group, a substituted or unsubstituted amine group, a substituted or unsubstituted $C_1$-$C_6$ alkyl group, a substituted or unsubstituted $C_1$-$C_6$ alkoxy group, a substituted or unsubstituted $C_3$-$C_{10}$ cycloalkyl, and a substituted or unsubstituted heterocycloalkyl;

$X_1$, $X_2$, and $X_3$ are each independently —CR$_3$—, —O—, —S—, —N—, or —NR$_4$—;

' - - - - - ' is a single bond or a double bond;

Y is —(CH$_2$)$_a$—N(Q$_2$)(Q$_3$), —(CH$_2$)$_a$—O(Q$_2$), —(CH$_2$)$_a$—S(Q$_2$), —(CH$_2$)$_a$-Q$_2$, —(CH$_2$)$_a$—C(=O)(Q$_2$), —(CH$_2$)$_a$—N(Q$_2$)C(=O)-(Q$_3$), or —(CH$_2$)$_a$—C(=O)N(Q$_2$)(Q$_3$);

$Q_2$ and $Q_3$ are each independently selected from hydrogen, a $C_1$-$C_6$ alkyl group, a $C_2$-$C_6$ alkenyl group, a $C_2$-$C_6$ alkynyl group, a $C_3$-$C_{10}$ cycloalkyl, a $C_1$-$C_{10}$ heterocycloalkyl, a $C_1$-$C_{12}$ biheterocycloalkyl, a $C_1$-$C_{18}$ triheterocycloalkyl, a $C_1$-$C_{12}$ spiroheterocycloalkyl, a $C_3$-$C_{12}$ aryl, and a $C_1$-$C_{12}$ heteroaryl, each of which may have one or more substituents selected from the group consisting of halogen, a cyano group, a hydroxyl group, a thiol group, a nitro group, a substituted or unsubstituted $C_1$-$C_6$ alkyl group, a substituted or unsubstituted $C_1$-$C_6$ alkoxy group, —(CH$_2$)$_a$—N(Q$_4$)(Q$_5$), —(CH$_2$)$_a$—O(Q$_4$), a substituted or unsubstituted $C_3$-$C_{10}$ aryl group, a substituted or unsubstituted $C_1$-$C_{10}$ heteroaryl group, a substituted or unsubstituted $C_3$-$C_{10}$ cycloalkyl group, and a substituted or unsubstituted $C_1$-$C_{10}$ heterocycloalkyl group;

$Q_4$ and $Q_5$ are each independently selected from hydrogen, a $C_1$-$C_6$ alkyl group, a $C_2$-$C_6$ alkenyl group, and a $C_2$-$C_6$ alkynyl group;

a is an integer from 0 to 6;

$R_3$ is selected from hydrogen, a halogen, a cyano group, a hydroxyl group, a thiol group, a nitro group, a substituted or unsubstituted amine group, a substituted or unsubstituted amide group, a substituted or unsubstituted ester group, a substituted or unsubstituted $C_1$-$C_6$ alkyl group, a substituted or unsubstituted $C_3$-$C_{10}$ cycloalkyl group, a substituted or unsubstituted $C_1$-$C_6$ alkoxy group, and a $C_1$-$C_6$ alkoxy group substituted with one or more halogens;

$R_4$ is hydrogen or a substituted or unsubstituted $C_1$-$C_6$ alkyl group; and the substituents may each independently be selected from a halogen, a cyano group, a hydroxyl group, a thiol group, an oxo, a nitro group, a $C_1$-$C_6$ alkyl group, a $C_2$-$C_6$ alkenyl group, a $C_2$-$C_6$ alkynyl group, a $C_1$-$C_6$ alkoxy group, a $C_3$-$C_{10}$ cycloalkyl group, a $C_1$-$C_{10}$ heterocycloalkyl group, a $C_3$-$C_{10}$ cycloalkoxy group, a $C_3$-$C_{10}$ aryloxy group, a $C_3$-$C_{10}$ arylthiol group, a $C_1$-$C_{10}$ heteroaryloxy group, a $C_1$-$C_{10}$ heteroarylthiol group, a $C_3$-$C_{10}$ aryl group, and a $C_1$-$C_{10}$ heteroaryl group.

The term "halogen" as used herein may be F, C$_1$, Br, or I.

The term "alkyl" as used herein refers to a straight-chain or branched hydrocarbon residue, which may be substituted or unsubstituted, unless stated otherwise. The alkyl group may include, without limitation, all possible isomers thereof such as, for example, methyl, ethyl, propyl, butyl, pentyl, hexyl, or isopropyl, isobutyl, and t-butyl.

Unless stated otherwise, the term "alkoxy" as used herein refers to a straight-chain or branched hydrocarbon residue, which may be substituted or unsubstituted, linked with oxygen. For example, the alkoxy may include, without limitation, methoxy, ethoxy, propoxy, and butoxy, or all possible isomers thereof such as isopropoxy, isobutoxy, and t-butoxy.

The term "alkenyl" as used herein refers to an unsaturated aliphatic group that is similar in length and substitutability to the above-described alkyl, but contains one or more carbon-carbon double bonds. For example, the alkenyl may include ethenyl, propenyl, butenyl, pentenyl, hexenyl, and branched alkenyl groups, or all isomers thereof such as (E) or (Z) without limitation.

The term "alkynyl" as used herein refers to an unsaturated aliphatic group that is similar in length and substitutability to the above-described alkyl, but contains one or more carbon-carbon triple bonds. For example, the alkynyl may include ethynyl, propynyl, butynyl, pentynyl, hexynyl, and branched alkynyl groups without limitation.

Unless stated otherwise, the term "cycloalkyl" as used herein has the same meaning as "carbocycloalkyl," and refers to cyclic alkyl that may be substituted or unsubstituted. The cycloalkyl group may include, for example, a $C_3$-$C_{30}$ carbocycloalkyl, a $C_3$-$C_{20}$ carbocycloalkyl, or a $C_3$-$C_{10}$ carbocycloalkyl, such as mono-, bridged cyclic groups (e.g. bicycloaliphatic or tricycloalkyl) or spirobicyclic groups. Specifically, unless stated otherwise, the term "bicycloalkyl" or "tricycloalkyl" as used herein, which is a type of "polycycloalkyl," refers to a structure consisting of two or more cycloalkyl moieties having two or more atoms in common. For example, the carbocycloalkyl group may include cyclopropyl, cyclobutyl, cyclopentyl, cyclohexyl, cyclohexenyl, cycloheptyl, cycloheptenyl, cyclooctyl, cyclooctenyl, 2,5-cyclohexadienyl, bicyclo[2.2.1]heptyl, bicyclo[2.2.2]octyl, adamant-1-yl, decahydronaphthyl, oxocyclohexyl, dioxocyclohexyl, thiocyclohexyl, 2-oxobicyclo[2.2.1]hept-1-yl, spiro[5.5]undecane, or any possible isomers thereof without limitation.

Unless stated otherwise, the term "heterocycloalkyl" as used herein refers to a monocyclic, bicyclic, tricyclic or greater, or spirobicyclic substituted or unsubstituted cyclic aryl or alkyl including one or more heteroatoms selected from B, N, O, S, P(=O), Si, and P. Examples of mono heterocycloalkyl include, but are not limited to, piperidinyl, morpholinyl, thiomorpholinyl, pyrrolidinyl, imidazolidinyl, tetrahydrofuryl, piperazinyl, and other similar groups. Examples of biheterocycloalkyl include, but are not limited to, diaza bicyclo[2.2.1]heptyl, hexahydropyrrolo[3,4-c]pyrrolo, and other similar groups. In addition, examples of spiroheterocycloalkyl include, but are not limited to, diazaspiro[5.5]undecane, diazaspiro[4.5]decane, diazaspiro[4.4]nonane, diazaspiro[3.5]nonane, diazaspiro[3.3]heptane, diazaspiro[3.4]octane, 3-oxa-9-azaspiro[5.5]undecane, 2-oxa-7-azaspiro[3.5]nonane, and other similar groups.

The term "aryl" as used herein refers to, unless stated otherwise, an aromatic group that may be substituted or unsubstituted, and may include, for example, $C_6$-$C_{30}$ aryl, $C_6$-$C_{20}$ aryl, or $C_6$-$C_{10}$ aryl, and double bonds alternate (resonate) between adjacent carbon atoms or suitable heteroatoms. For example, aryl may include phenyl, biphenyl, naphthyl, toluyl, naphthalenyl, anthracenyl, or any possible isomers thereof without limitation.

Unless stated otherwise, the term "heteroaryl" as used herein refers to monocyclic or bicyclic or greater, substituted or unsubstituted aromatic group including one or more heteroatoms selected from B, N, O, S, P(=O), Si, and P. Examples of monocyclic heteroaryl are, but not limited to, thiazolyl, oxazolyl, thiophenyl, furanyl, pyrrolyl, imidazolyl, isoxazolyl, pyrazolyl, triazolyl, thiadiazolyl, tetrazolyl, oxadiazolyl, pyridinyl, pyridazinyl, pyrimidinyl, pyrazinyl, thiazolyl, and other similar groups. Examples of bicyclic heteroaryl are, but not limited to, indolyl, benzothiophenyl, benzofuranyl, benzimidazolyl, benzoxazolyl, benzisoxazolyl, benzthiazolyl, benzthiadiazolyl, benztriazolyl, quinolinyl, isoquinolinyl, purinyl, puropyridinyl, oxochromene, dioxoisoindolin, pyrazolopyridinyl, pyrazolo[1,5-a]pyridinyl, and other similar groups.

The term "amine" or "amino" as used herein may be represented by the formula of —NA1A2A3, wherein A1, A2, and A3 are each independently hydrogen or a substituted or unsubstituted alkyl, cycloalkyl, alkenyl, cycloalkenyl, alkynyl, cycloalkynyl, aryl, or heteroaryl group as defined above.

The term "ester" as used herein may be represented by the formula of —OC(O)A1 or —C(O)OA1, wherein A1 may be a substituted or unsubstituted alkyl, cycloalkyl, alkenyl, cycloalkenyl, alkynyl, cycloalkynyl, aryl, or heteroaryl group as defined above.

The term "amide" as used herein may be represented by the formula —NHC(O)A1 or —C(O)NHA1, wherein A1 may be hydrogen or a substituted or unsubstituted alkyl, cycloalkyl, alkenyl, cycloalkenyl, alkynyl, cycloalkynyl, aryl, or heteroaryl group as defined above.

Any numerical range expressed with "to" as herein may refer to a range including the figures before and after the expression "to" as the lower and upper limits, respectively.

The term "solvate" as used herein may include a molecular composite including a compound and at least one pharmaceutically acceptable solvent molecule, for example, ethanol or water. A composite including water as the solvent molecule is also referred to as "hydrate."

The term "derivative" as used herein refers to a compound obtained by substitution part of the structure of the compound with a different atom or atomic group.

In addition, the compound according to the present invention may be used in the form of a pharmaceutically acceptable salt derived from an inorganic acid or an organic acid. For example, the salt may be a salt derived from hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid, toluenesulfonic acid, or the like.

A pharmaceutically acceptable salt of the compound according to the present invention may be prepared by dissolving the compound of Formula 1 in a water-miscible organic solvent, for example, acetone, methanol, ethanol, or acetonitrile, adding an excess of organic acid or an aqueous acid solution of inorganic acid, and thereafter precipitation or crystallization. Subsequently, after evaporation of the solvent or excess of acid from this mixture, the resulting product is dried to thereby obtain an addition salt or the precipitated salt may then be filtered by suction to thereby prepare a pharmaceutically acceptable salt.

In an embodiment, in Formula I, Xi may be —CH—, —O—, —S—, —N—, or —NH—;

$X_2$ may be —CH— or —N—; $X_3$ may be —$CR_3$—, —O—, —S—, —N—, or —$NR_4$—; $R_3$ may be hydrogen, a halogen, a cyano group, a hydroxyl group, a thiol group, a nitro group, a substituted or unsubstituted amine group, a substituted or unsubstituted amide group, a substituted or unsubstituted ester group, a substituted or unsubstituted $C_1$-$C_6$ alkyl group, a substituted or unsubstituted $C_3$-$C_{10}$ cycloalkyl group, a substituted or unsubstituted $C_1$-$C_6$ alkoxy group, or a $C_1$-$C_6$ alkoxy group substituted with one or more halogens; and $R_4$ may be hydrogen or a $C_1$-$C_6$ alkyl group.

In an embodiment, in Formula I, Xi may be —CH— or —NH—; $X_2$ may be —CH— or —N—; $X_3$ may be —$CR_3$—, —O—, —S—, or —N—; and $R_3$ may be hydrogen, a halogen, a cyano group, or a $C_1$-$C_6$ alkyl group.

In an embodiment, in Formula I, $R_1$ and $R_2$ may each independently be selected from among a substituted or unsubstituted $C_1$-$C_6$ alkyl group or a substituted or unsubstituted $C_3$-$C_{10}$ cycloalkyl group; $Cy_1$ may be phenyl or pyridine; and $Cy_1$ may be phenyl, pyridine, or pyrazole, each of which may have one or more substituents selected from the group consisting of a hydroxyl group, a halogen, and a $C_1$-$C_6$ alkyl group.

In an embodiment, in Formula I, Y may be —$(CH_2)_a$-$Q_2$, —$N(Q_2)(Q_3)$, —$N(Q_2)C(=O)$-$(Q_3)$, or —$C(=O)N(Q_2)(Q_3)$, $Q_2$ and $Q_3$ may each independently be selected from among hydrogen, a $C_1$-$C_6$ alkyl group, a $C_3$-$C_{10}$ cycloalkyl, a $C_1$-$C_{10}$ heterocycloalkyl, a $C_1$-$C_{12}$ biheterocycloalkyl, a $C_1$-$C_{12}$ spiroheterocycloalkyl, a $C_3$-$C_{12}$ aryl, and a $C_1$-$C_{12}$ heteroaryl, each of which may have one or more substituents selected from the group consisting of halogen, a substituted or unsubstituted $C_1$-$C_6$ alkyl group, —$(CH_2)_a$—$N(Q_4)(Q_5)$, —$(CH_2)_a$—$O(Q_4)$, a substituted or unsubstituted $C_3$-$C_{10}$ cycloalkyl group, and a substituted or unsubstituted $C_1$-$C_{10}$ heterocycloalkyl group; and $Q_4$ and $Q_5$ may each independently be hydrogen or a $C_1$-$C_6$ alkyl group.

In an embodiment, the compound represented by Formula I may be selected from the group consisting of compounds 1) to 67):

1) N-methyl-N-(2-((2-((4-(4-methylpiperazin-1-yl)phenyl)amino)-7H-pyrrolo[2,3-d]pyrimidine-4-yl)amino)phenyl)methanesulfonamide;
2) N-methyl-N-(2-((2-((2-methyl-4-(4-methylpiperazin-1-yl)phenyl)amino)-7H-pyrrolo[2,3-d]pyrimidine-4-yl)amino)phenyl)methanesulfonamide;
3) N-(2-((2-((2-fluoro-4-(4-methylpiperazin-1-yl)phenyl)amino)-7H-pyrrolo[2,3-d]pyrimidine-4-yl)amino)phenyl)-N-methylmethanesulfonamide;
4) N-(2-((2-((3-hydroxy-4-(4-methylpiperazin-1-yl)phenyl)amino)-7H-pyrrolo[2,3-d]pyrimidine-4-yl)amino)phenyl)-N-methylmethanesulfonamide;
5) N-methyl-N-(2-((2-((3-methyl-4-(4-methylpiperazin-1-yl)phenyl)amino)-7H-pyrrolo[2,3-d]pyrimidine-4-yl)amino)phenyl)methanesulfonamide;
6) N-(2-((2-((3-chloro-4-(4-methylpiperazin-1-yl)phenyl)amino)-7H-pyrrolo[2,3-d]pyrimidine-4-yl)amino)phenyl)-N-methylmethanesulfonamide;
7) N-(2-((2-((3-fluoro-4-(4-methylpiperazin-1-yl)phenyl)amino)-7H-pyrrolo[2,3-d]pyrimidine-4-yl)amino)phenyl)-N-methylmethanesulfonamide;
8) N-(2-((2-((3-fluoro-4-(4-ethylpiperazin-1-yl)phenyl)amino)-7H-pyrrolo[2,3-d]pyrimidine-4-yl)amino)phenyl)-N-methylmethanesulfonamide;
9) N-(2-((2-((3-fluoro-4-(4-isopropylpiperazin-1-yl)phenyl)amino)-7H-pyrrolo[2,3-d]pyrimidine-4-yl)amino)phenyl)-N-methylmethanesulfonamide;
10) N-(2-((2-((3-fluoro-4-(4-propylpiperazin-1-yl)phenyl)amino)-7H-pyrrolo[2,3-d]pyrimidine-4-yl)amino)phenyl)-N-methylmethanesulfonamide;
11) N-(2-((2-((3-fluoro-4-(4-cyclopropylpiperazin-1-yl)phenyl)amino)-7H-pyrrolo[2,3-d]pyrimidine-4-yl)amino)phenyl)-N-methylmethanesulfonamide;
12) N-(2-((2-((3-fluoro-4-morpholinophenyl)amino)-7H-pyrrolo[2,3-d]pyrimidine-4-yl)amino)phenyl)-N-methylmethanesulfonamide;
13) N-(2-((2-((3-fluoro-4-(4-(4-methylpiperazin-1-yl)piperidin-1-yl)phenyl)amino)-7H-pyrrolo[2,3-d]pyrimidine-4-yl)amino)phenyl)-N-methylmethanesulfonamide;
14) N-(2-((2-((3-fluoro-4-(4-(4-ethylpiperazin-1-yl)piperidin-1-yl)phenyl)amino)-7H-pyrrolo[2,3-d]pyrimidine-4-yl)amino)phenyl)-N-methylmethanesulfonamide;
15) N-(2-((2-((3-fluoro-4-(4-(4-isopropylpiperazin-1-yl)piperid in-1-yl)phenyl)amino)-7H-pyrrolo[2,3-d]pyrimidine-4-yl)amino)phenyl)-N-methylmethanesulfonamide;
16) N-(2-((2-((3-fluoro-4-(4-(4-propylpiperazin-1-yl)piperidin-1-yl)phenyl)amino)-7H-pyrrolo[2,3-d]pyrimidine-4-yl)amino)phenyl)-N-methylmethanesulfonamide;
17) N-(2-((2-((3-fluoro-4-(4-(4-cyclopropylpiperazin-1-yl)piperidin-1-yl)phenyl)amino)-7H-pyrrolo[2,3-d]pyrimidine-4-yl)amino)phenyl)-N-methylmethanesulfonamide;
18) N-(2-((2-((3-fluoro-4-(4-morpholinopiperidin-1-yl)phenyl)amino)-7H-pyrrolo[2,3-d]pyrimidine-4-yl)amino)phenyl)-N-methylmethanesulfonamide;
19) N-(2-((2-((3-fluoro-4-(4-(4-(oxetan-3-yl)piperazin-1-yl)piperidin-1-yl)phenyl)amino)-7H-pyrrolo[2,3-d]pyrimidine-4-yl)amino)phenyl)-N-methylmethanesulfonamide;
20) N-(2-((2-((3-fluoro-4-(1-methylpiperidin-4-yl)phenyl)amino)-7H-pyrrolo[2,3-d]pyrimidine-4-yl)amino)phenyl)-N-methylmethanesulfonamide;
21) N-(2-((2-((4-(4-(dimethylamino)piperidin-1-yl)-3-fluorophenyl)amino)-7H-pyrrolo[2,3-d]pyrimidine-4-yl)amino)phenyl)-N-methylmethanesulfonamide;
22) N-(2-((2-((4-(piperidin-1-yl)-3-fluorophenyl)amino)-7H-pyrrolo[2,3-d]pyrimidine-4-yl)amino)phenyl)-N-methylmethanesulfonamide;
23) N-(2-((2-((3-fluoro-4-(piperazin-1-yl)phenyl)amino)-7H-pyrrolo[2,3-d]pyrimidine-4-yl)amino)phenyl)-N-methylmethanesulfonamide;
24) N-(2-((2-((3-fluoro-4-((1-methylpiperidin-4-yl)amino)phenyl)amino)-7H-pyrrolo[2,3-d]pyrimidine-4-yl)amino)phenyl)-N-methylmethanesulfonamide;
25) N-(2-((2-((3,5-difluoro-4-(4-methylpiperazin-1-yl)phenyl)amino)-7H-pyrrolo[2,3-d]pyrimidine-4-yl)amino)phenyl)-N-methylmethanesulfonamide;
26) N-(2-((2-((4-(4-ethylpiperazin-1-yl)-3,5-difluorophenyl)amino)-7H-pyrrolo[2,3-d]pyrimidine-4-yl)amino)phenyl)-N-methylmethanesulfonamide;
27) N-(2-((2-((2,3-difluoro-4-(4-methylpiperazin-1-yl)phenyl)amino)-7H-pyrrolo[2,3-d]pyrimidine-4-yl)amino)phenyl)-N-methylmethanesulfonamide;
28) N-(2-((2-((2,3-difluoro-4-(4-(2-hydroxyethyl)piperazin-1-yl)phenyl)amino)-7H-pyrrolo[2,3-d]pyrimidine-4-yl)amino)phenyl)-N-methylmethanesulfonamide;
29) N-methyl-N-(2-((2-((5-(4-methylpiperazin-1-yl)pyridin-2-yl)amino)-7H-pyrrolo[2,3-d]pyrimidine-4-yl)amino)phenyl)methanesulfonamide;
30) N-methyl-N-(2-((2-((6-(4-methylpiperazin-1-yl)pyridin-3-yl)amino)-7H-pyrrolo[2,3-d]pyrimidine-4-yl)amino)phenyl)methanesulfonamide;
31) N-(2-((2-((3-fluoro-4-(9-methyl-3,9-diazaspiro[5.5]undecan-3-yl)phenyl)amino)-7H-pyrrolo[2,3-d]pyrimidine-4-yl)amino)phenyl)-N-methylmethanesulfonamide;

32) N-(2-((2-((4-(9-ethyl-3,9-diazaspiro[5.5]undecan-3-yl)-3-fluorophenyl)amino)-7H-pyrrolo[2,3-d]pyrimidine-4-yl)amino)phenyl)-N-methanesulfonamide;
33) N-(2-((2-((3-fluoro-4-(2-methyl-2,8-diazaspiro[4.5]decan-8-yl)phenyl)amino)-7H-pyrrolo[2,3-d]pyrimidine-4-yl)amino)phenyl)-N-methylmethanesulfonamide;
34) N-(2-((2-((3-fluoro-4-(2-methyl-2,7-diazaspiro[3.5]nonan-7-yl)phenyl)amino)-7H-pyrrolo[2,3-d]pyrimidine-4-yl)amino)phenyl)-N-methylmethanesulfonamide;
35) N-(2-((2-((3-fluoro-4-(8-methyl-2,8-diazaspiro[4.5]decan-2-yl)phenyl)amino)-7H-pyrrolo[2,3-d]pyrimidine-4-yl)amino)phenyl)-N-methylmethanesulfonamide;
36) N-(2-((2-((3-fluoro-4-(6-methyl-2,6-diazaspiro[3.3]heptan-2-yl)phenyl)amino)-7H-pyrrolo[2,3-d]pyrimidine-4-yl)amino)phenyl)-N-methylmethanesulfonamide;
37) N-(2-((2-((3-fluoro-4-(7-methyl-2,7-diazaspiro[3.5]nonan-2-yl)phenyl)amino)-7H-pyrrolo[2,3-d]pyrimidine-4-yl)amino)phenyl)-N-methylmethanesulfonamide;
38) N-(2-((2-((3-fluoro-4-(6-methyl-2,6-diazaspiro[3.4]octan-2-yl)phenyl)amino)-7H-pyrrolo[2,3-d]pyrimidine-4-yl)amino)phenyl)-N-methylmethanesulfonamide;
39) N-(2-((2-((3-fluoro-4-(3-oxa-9-diazaspiro[5.5]undecan-9-yl)phenyl)amino)-7H-pyrrolo[2,3-d]pyrimidine-4-yl)amino)phenyl)-N-methylmethanesulfonamide;
40) N-(2-((2-((3-fluoro-4-(2-oxa-7-azaspiro[3.5]nonan-7-yl)phenyl)amino)-7H-pyrrolo[2,3-d]pyrimidine-4-yl)amino)phenyl)-N-methylmethanesulfonamide;
41) N-(2-((2-((3-fluoro-4-((3aR,6aS)-5-methylhexahydropyrrolo[3,4-c]pyrrole-2(1H)-yl)phenyl)amino)-7H-pyrrolo[2,3-d]pyrimidine-4-yl)amino)phenyl)-N-methylmethanesulfonamide;
42) N-(2-((2-((3-fluoro-4-(4-methylpiperazin-1-yl)phenyl)amino)-7H-pyrrolo[2,3-d]pyrimidine-4-yl)amino)phenyl)methanesulfonamide;
43) N-ethyl-N-(2-((2-((3-fluoro-4-(4-methylpiperazin-1-yl)phenyl)amino)-7H-pyrrolo[2,3-d]pyrimidine-4-yl)amino)phenyl)methanesulfonamide;
44) N-(2-((2-((3-fluoro-4-(4-methylpiperazin-1-yl)phenyl)amino)-7H-pyrrolo[2,3-d]pyrimidine-4-yl)amino)phenyl)-N-isopropylmethanesulfonamide;
45) N-cyclopropyl-N-(2-((2-((3-fluoro-4-(4-methylpiperazin-1-yl)phenyl)amino)-7H-pyrrolo[2,3-d]pyrimidine-4-yl)amino)phenyl)methanesulfonamide;
46) N-(2-((2-((3-fluoro-4-(4-methylpiperazin-1-yl)phenyl)amino)-7H-pyrrolo[2,3-d]pyrimidine-4-yl)amino)phenyl)-N-methylethanesulfonamide;
47) N-(2-((2-((3-fluoro-4-(4-methylpiperazin-1-yl)phenyl)amino)-7H-pyrrolo[2,3-d]pyrimidine-4-yl)amino)phenyl)-N-methylpropan-2-sulfonamide;
48) N-(2-((2-((3-fluoro-4-(4-methylpiperazin-1-yl)phenyl)amino)-7H-pyrrolo[2,3-d]pyrimidine-4-yl)amino)phenyl)-N-methylcyclopropanesulfonamide;
49) N-(2-((2-((4-(4-ethylpiperazin-1-yl)-3-fluorophenyl)amino)-7H-pyrrolo[2,3-d]pyrimidine-4-yl)amino)phenyl)methanesulfonamide;
50) N-ethyl-N-(2-((2-((4-(4-ethylpiperazin-1-yl)-3-fluorophenyl)amino)-7H-pyrrolo[2,3-d]pyrimidine-4-yl)amino)phenyl)methanesulfonamide;
51) N-(2-((2-((4-(4-ethylpiperazin-1-yl)-3-fluorophenyl)amino)-7H-pyrrolo[2,3-d]pyrimidine-4-yl)amino)phenyl)-N-methylethanesulfonamide;
52) N-ethyl-N-(2-((2-((4-(4-ethylpiperazin-1-yl)-3-fluorophenyl)amino)-7H-pyrrolo[2,3-d]pyrimidine-4-yl)amino)phenypethanesulfonamide;
53) N-(2-((2-((4-(4-(4-ethylpiperazin-1-yl)piperidin-1-yl)-3-fluorophenyl)amino)-7H-pyrrolo[2,3-d]pyrimidine-4-yl)amino)phenyl)methanesulfonamide;
54) N-(2-((2-((4-(4-(4-ethylpiperazin-1-yl)piperidin-1-yl)-3-fluorophenyl)amino)-7H-pyrrolo[2,3-d]pyrimidine-4-yl)amino)phenyl)-N-methylethanesulfonamide;
55) N-ethyl-N-(2-((2-((4-(9-ethyl-3,9-diazaspiro[5.5]undecan-3-yl)-3-fluorophenyl)amino)-7H-pyrrolo[2,3-d]pyrimidine-4-yl)amino)phenyl)methanesulfonamide;
56) N-(2-((2-((4-(2-ethyl-2,8-diazaspiro[4.5]decan-8-yl)-3-fluorophenyl)amino)-7H-pyrrolo[2,3-d]pyrimidine-4-yl)amino)phenyl)-N-methylethanesulfonamide;
57) N-(2-((5-chloro-2-((3-fluoro-4-(4-methylpiperazin-1-yl)phenyl)amino)-7H-pyrrolo[2,3-d]pyrimidine-4-yl)amino)phenyl)-N-methylmethanesulfonamide;
58) N-(2-((5-chloro-2-((2,3-difluoro-4-(4-methylpiperazin-1-yl)phenyl)amino)-7H-pyrrolo[2,3-d]pyrimidine-4-yl)amino)phenyl)-N-methylmethanesulfonamide;
59) N-(2-((5-chloro-2-((6-(4-methylpiperazin-1-yl)pyridin-3-yl)amino)-7H-pyrrolo[2,3-d]pyrimidine-4-yl)amino)phenyl)-N-methylmethanesulfonamide;
60) N-(2-((2-((3-fluoro-4-(4-methylpiperazin-1-yl)phenyl)amino)-5-methyl-7H-pyrrolo[2,3-d]pyrimidine-4-yl)amino)phenyl)-N-methylmethanesulfonamide;
61) N-(2-((5-cyano-2-((3-fluoro-4-(4-methylpiperazin-1-yl)phenyl)amino)-7H-pyrrolo[2,3-d]pyrimidine-4-yl)amino)phenyl)-N-methylmethanesulfonamide;
62) N-(2-((5-fluoro-2-((3-fluoro-4-(4-methylpiperazin-1-yl)phenyl)amino)-7H-pyrrolo[2,3-d]pyrimidine-4-yl)amino)phenyl)-N-methylmethanesulfonamide;
63) N-(2-((2-((4-(4-ethylpiperazin-1-yl)-3-fluorophenyl)amino)-5-fluoro-7H-pyrrolo[2,3-d]pyrimidine-4-yl)amino)phenyl)-N-methylmethanesulfonamide
64) N-(2-((5-fluoro-2-((3-fluoro-4-(4-(4-methylpiperazin-1-yl)piperidin-1-yl)phenyl)amino)-7H-pyrrolo[2,3-d]pyrimidine-4-yl)amino)phenyl)-N-methylmethanesulfonamide;
65) N-(2-((2-((3-fluoro-4-(4-(4-methylpiperazin-1-yl)piperidin-1-yl)phenyl)amino)-7-methyl-7H-pyrrolo[2,3-d]pyrimidine-4-yl)amino)phenyl)-N-methylmethanesulfonamide;
66) N-methyl-N-(2-((2-((1-(1-methylpiperidin-4-yl)-1H-pyrazol-4-yl)amino)-7H-pyrrolo[2,3-d]pyrimidine-4-yl)amino)phenyl)methanesulfonamide; and
67) N-(2-((2-((3-fluoro-4-(4-methylpiperazin-1-yl)phenyl)amino)-9H-purin-6-yl)amino)phenyl)-N-methylmethanesulfonamide.

Another aspect relates to a pharmaceutical composition including, as an active ingredient, the compound of Formula I, a solvate or stereoisomer thereof, or a pharmaceutically acceptable salt thereof.

In one embodiment, the pharmaceutical composition may be a pharmaceutical composition for preventing or treating cancer.

In one embodiment, the pharmaceutical composition may be a pharmaceutical composition for preventing or treating cancer having an EGFR mutation.

In one embodiment, provided is a pharmaceutical composition, wherein the EGFR mutation is an activating EGFR mutation, a mutation causing resistance to an EGFR inhibitor, or a combination thereof.

Another aspect relates to pharmaceutical use of the compound of Formula I, a solvate or stereoisomer thereof, or a pharmaceutically acceptable salt thereof.

The pharmaceutical use may be preventive or therapeutic use for cancer, specifically, preventive or therapeutic use for cancer having an EGFR mutation. More specifically, the EGFR mutation may be an activating EGFR mutation, a mutation causing resistance to an EGFR inhibitor, or a combination thereof.

The compound of formula (I) may inhibit the proliferation of cancer cells, particularly cancer cells caused by mutations in the tyrosine kinase domain of epidermal growth factor receptors (EGFR), inhibit the expression of resistance to EGFR inhibitor drugs, or selectively and effectively inhibit cancer having resistance to such EGFR inhibitory drugs.

This effect was proved in Experimental Examples 1, 2 and 3 below. In order to identify whether the compound exhibits activity against cells expressing an EGFR mutation, a growth inhibitory effect was identified in Ba/F3 and PC9 cell lines overexpressing EGFR del19/T790M/C797S mutations (Experimental Examples 1 and 2). As a result (Tables 5 and 6), the compound of Formula I exhibited a very excellent proliferation inhibitory effect in the Ba/F3 and PC9 cell lines. In contrast, erlotinib and osimertinib, which are conventional EGFR inhibitor drugs, had an extremely insignificant inhibitory effect on the proliferation of the Ba/F3 cell lines. Afatinib exhibited an inhibitory effect on the proliferation of Ba/F3 cell lines, but at the same time, it is known to have a remarkable inhibitory effect on EGFR WT, causing serious side effects (diarrhea, skin disease, and weight loss).

In order to evaluate the possibility of side effects caused by such inhibition of EGFR WT, the compound according to the present invention was evaluated for selectivity in EGFR WT and mutations (Experimental Example 3). As a result (Table 7), the compound of Formula I exhibited an excellent enzyme inhibitory effect against EGFR L858R/T790M/C797S and L858R/T790M mutations, but did not exhibit an enzyme inhibitory effect against EGFR WT. Thus, the compound of Formula I exhibited very high selectivity for EGFR mutations and was found to have remarkably superior selectivity as compared to afatinib.

Therefore, it was confirmed that the compound of Formula I is a safer and more effective drug for patients with non-small cell lung cancer with EGFR mutation.

In one embodiment, the cancer may be selected from the group consisting of lung cancer, liver cancer, esophageal cancer, gastric cancer, colon cancer, small intestine cancer, pancreatic cancer, melanoma, breast cancer, oral cancer, brain tumor, thyroid cancer, parathyroid cancer, kidney cancer, cervical cancer, sarcoma, prostate cancer, urethra cancer, bladder cancer, testicular cancer, hematologic cancer, lymphoma, skin cancer, psoriasis, and fibroadenoma.

In one embodiment, the cancer may be non-small cell lung cancer.

In addition, the pharmaceutical composition according to the present invention may be administered alone or in combination with one or more additional therapeutic agents. The term "administration in combination" means administration of a pharmaceutical composition according to an aspect and one or more additional therapeutic agents to an individual or patient being treated, simultaneously or at different points of time with a time difference in any order. Accordingly, each component may be administered separately or may be administered in a sufficiently approximate time to provide a desired therapeutic effect. The one or more additional therapeutic agents may be, for example, other anticancer agents.

The dosage of the pharmaceutical composition is an amount effective for the treatment or prevention in an individual or patient, and can be administered orally or parenterally as desired. When administered orally, 0.01 to 1000 mg per 1 kg of body weight a day, and more specifically, 0.1 to 300 mg, on the basis of the active ingredient, may be administered. When administered parenterally, it may be administered in divided doses from 1 to several times so as to be administered in an amount of 0.01 to 100 mg, more specifically 0.1 to 50 mg per 1 kg of body weight a day. It will be understood that the dosage of administration to a specific individual or patient should be determined in light of a number of related factors such as the patient's weight, age, sex, health status, diet, administration time, administration method, and disease severity, and can be appropriately increased or reduced by a specialist. The above-described dosage is not intended to limit the scope of the present invention in any aspect. A physician or veterinarian having ordinary skill in the related art can readily determine and prescribe a desired effective amount of pharmaceutical composition. For example, a doctor or veterinarian may determine a dosage of the compound according to an embodiment for use in a pharmaceutical composition, starting from a level lower than that required to achieve a desired therapeutic effect, to gradually increase the dosage until the desired effect is achieved.

In one embodiment, the pharmaceutical composition may include a pharmaceutically acceptable carrier, an excipient, or an additive, which are commonly used in the art. The pharmaceutical composition according to the present invention can be formulated according to a common method used in the art, and may be prepared in a variety of oral dosage forms such as tablets, pills, powders, capsules, syrups, emulsions, microemulsions, or in parenteral dosage forms such as for intramuscular, intravenous or subcutaneous administration.

When the pharmaceutical composition according to the present invention is prepared in an oral dosage form, examples of a suitable additive or carrier include cellulose, calcium silicate, corn starch, lactose, sucrose, dextrose, calcium phosphate, stearic acid, magnesium stearate, calcium stearate, gelatin, talc, surfactants, suspending agents, emulsifying agents, diluents, and the like. When the pharmaceutical composition according to the present invention is prepared as an injection, the additive or carrier may include water, saline, aqueous glucose solutions, aqueous sugar-like solutions, alcohols, glycols, ethers (e.g., polyethylene glycol 400), oils, fatty acids, fatty acid esters, glycerides, surfactants, suspending agents, emulsifying agents, and the like.

Another aspect provides a method of preventing or treating cancer, the method comprising administering the compound of Formula 1, a solvate or stereoisomer thereof, or a pharmaceutically acceptable salt thereof, in a therapeutically effective amount to an individual or patient in need of cancer treatment.

For details of the preventing or treating method, the above description of the pharmaceutical composition according to an aspect of the present invention may be applied as it is.

In addition, for the dosage that applies to the preventing or treating method, which is an amount effective for treating or preventing an individual or patient, the above-description of the dosage of the pharmaceutical composition may be applied as it is.

The term "treating" or "treatment" as used herein refers to: inhibition of disease, for example, inhibition of a disease, condition or disorder in an individual experiencing or showing a pathology or symptom of a disease, condition or disorder, i.e., preventing a further onset of pathology and/or symptoms; or ameliorating disease, for example, ameliorating a disease, condition or disorder in an individual experiencing or exhibiting a pathology or symptom of a disease, condition or disorder, i.e., reversing pathology and/or symptoms, for example, reducing disease severity.

The term "preventing" or "prevention" as used herein refers to preventing disease, for example, a disease, condition or disorder in an individual who is predisposed to a disease, condition or disorder, but has not yet experienced or exhibited the pathology or signs of the disease.

The term "individual" or "patient" as used herein refers to any animals, including mammals, for example, mice, rats, other rodents, rabbits, dogs, cats, pigs, cows, sheep, horses, or primates, and humans.

Another aspect provides a compound library comprising one or more of the compound according to the present invention, and salts, isomers, hydrates, and solvates thereof.

Hereinafter, a method of preparing the compound of Formula I will be described in detail.

Typically, the compound of Formula 1 may be prepared according to a method shown in Reaction scheme 1, but embodiments are not limited thereto. The compound of Formula 1 may also be prepared by those of ordinary skill in the field of organic compounds using any methods other than methods specified in the following examples, by appropriately controlling specific reaction pathways, reaction conditions, reaction amounts, and the like.

[Reaction scheme 1]

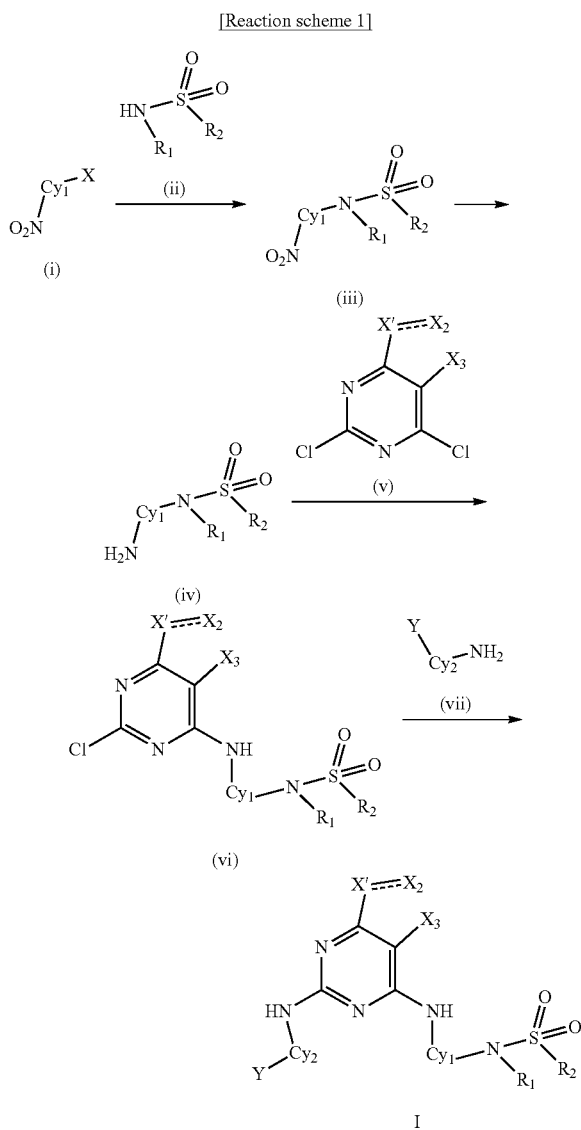

In Reaction scheme 1,

X is halogen, X' is $X_1$ or $X_1$ substituted with a protecting group such as p-toluenesulfonyl, (2-(trimethylsilyl)ethoxy) methyl or tetrahydropyran-2-yl, and $Cy_1$, $Cy_2$, $R_1$, $R_2$, $X_1$, $X_2$, $X_3$, and Y are as defined in Formula I.

When described in more detail with reference to Reaction scheme 1, a compound (iii) in which sulfonamide is substituted may be obtained from a commercially available halogen-substituted compound (I) by reaction with a sulfonamide compound (ii) in which $R_1$ and $R_2$ are substituted, in a solvent such as acetonitrile or N,N-dimethylformamide under a basic condition such as cesium carbonate or sodium hydride at a temperature ranging from room temperature to 100° C. Here, the sulfonamide compound (ii) as used in the reaction may be commercially purchased, or may be prepared for use by reacting a commercially available amine compound substituted with $R_1$ and a sulfonyl chloride compound substituted with $R_2$, in a solvent such as pyridine, water, tetrahydrofuran or dichloromethane under 1,8-diazabicyclo[5.4.0]undec-7-ene and a basic condition at an appropriate strength of 4-dimethylaminopyridine, potassium carbonate, triethylamine, or N,N-diisopropylethylamine at a temperature ranging from room temperature to 60° C.

Compound (iv) may be obtained by converting a nitro group of the prepared compound (iii) into an amine through a hydrogenation reaction using palladium/carbon as a catalyst or an iron-mediated reduction reaction.

The prepared compound (iv) is reacted with a fused pyrimidine compound (v) in a solvent such as butanol or N,N-dimethylformamide using a base at an appropriate strength such as N,N-diisopropylethylamine or tert-butoxypotassium at a temperature ranging from room temperature to 100° C. to obtain a sulfonamide compound (vi) in which the chloride at the 4 position of the fused pyrimidine is substituted with an amine. Here, the fused pyrimidine compound (v) as used in the reaction may be commercially purchased, or the fused pyrimidine compound (v) in which X' is $X_1$ having a protecting group such as p-toluenesulfonyl, (2-(trimethylsilyl)ethoxy)methyl or tetrahydropyran-2-yl may be prepared and used, for example, when $X_1$ is NH, by reacting p-toluene sulfonyl chloride or 2-(trimethylsilyl) ethoxymethyl chloride with triethylamine in a solvent such as dichloromethane or N,N-dimethylformamide under a basic condition such as 4-methylaminopyridine or sodium hydride at a temperature ranging from room temperature to 100° C., or by reacting dihydropyran in a solvent such as dichloromethane or tetrahydrofuran under an acid condition such as p-toluenesulfonic acid at a temperature ranging from room temperature to 100° C.

The prepared compound (vi) and an amine compound (vii) may be reacted in an alcoholic solvent such as 2-butanol in the presence of an inorganic acid such as hydrochloric acid or an organic acid such as p-toluenesulfonic acid or trifluoroacetic acid at a temperature ranging from 70° C. to reflux temperature, or may be reacted in an organic solvent such as 2-butanol or 1,4-dioxane in the presence of a palladium catalyst such as tris(dibenzylideneacetone)dipalladium(0), a ligand such as (±)-2,2'-bis(diphenylphosphino)-1,1'-binapthyl (BINAP) or 2-dicyclohexylphosphino-2',4',6'-triisopropyl biphenyl (Xphos), and an inorganic base such as cesium carbonate, potassium carbonate or tert-butoxysodium in a temperature range of about 100° C., to thereby obtain a compound of Formula 1 according to the present invention in which a halogen at position 2 of the fused pyrimidine is substituted with an amine. When X' is $X_1$ having a protecting group such as p-toluenesulfonyl, (2-(trimethylsilyl)ethoxy)methyl or tetrahydropyran-2-yl, the compound of Formula 1 according to the present invention may be obtained by reaction in a solvent such as tetrahydrofuran, methanol or methylene chloride in an acidic condition such as trifluoroacetic acid or in a basic condition such as tetrabutylammonium fluoride or sodium hydride aqueous solution, or sequentially in such an acid condition and a basic condition to cause a deprotection reaction. Here, the amine compound (vii) as used in the reaction may be obtained in a manner as in Reaction scheme 2.

[Reaction scheme 2]

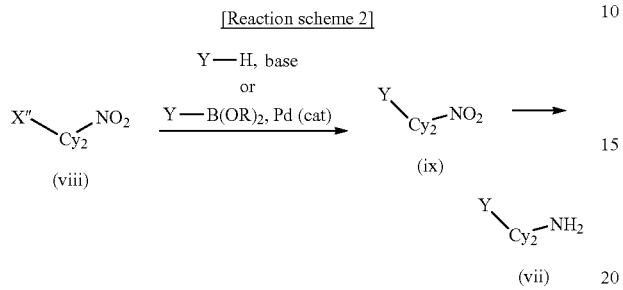

Reaction scheme 2 is a reaction scheme for the preparation of an intermediate compound (vii).

In Reaction scheme 2,

Cy2 and Y are as defined above in Formula (I), X" is halogen, and R is H or a substituted or unsubstituted alkyl. When R is alkyl, two Rs may form a fused ring.

When described in more detail with reference to Reaction scheme 2, compound (ix) in which the halogen of compound (viii) is substituted with Y may be obtained from a commercially available halogen-substituted nitro compound (viii) by reaction with a commercially available Y—H in a solvent such as N,N-dimethylformamide or acetonitrile under a basic condition such as potassium carbonate at a temperature ranging from room temperature to 100° C., or by reaction with the same in an organic solvent such as 1,4-dioxane in the presence of a palladium catalyst such as palladium(II)acetate, a ligand such as (4,5-bis(diphenylphosphino)-9,9-dimethylxanthene (Xantphos), and an inorganic base such as cesium carbonate in a temperature range of about 100° C. Alternatively, as a synthesis method under different conditions, compound (ix) may be obtained by coupling compound (viii) with boronic acid or boronate ester Y—B(OR)$_2$ under Suzuki conditions. Typically this reaction is performed by heating a halogen compound with boronic acid or boronate ester in a solvent such as N,N-dimethylformamide in the presence of a base such as potassium carbonate and a palladium catalyst such as 1,1"-bis(diphenylphosphino)ferrocene]dichloropalladium(II) dichloromethane complex at a temperature of about 80° C. to about 100° C. The boronic acid or boronate ester Y—B(OR)$_2$ as used herein may be commercially purchased or may be obtained by coupling a Y-substituted halogen compound with boronate ester dimer.

Compound (vii) may be obtained by converting the nitro group of the prepared compound (ix) into an amine through a hydrogenation reaction using palladium/carbon as a catalyst or an iron-mediated reduction reaction.

A pharmaceutical composition including, as an active ingredient, the compound of Formula I, a solvate or stereoisomer thereof, or a pharmaceutically acceptable salt thereof, synthesized by a preparation method as above, may be used to inhibit the growth of cancer cells and resistance to drugs, which are induced by mutation in the tyrosine kinase domain of epithelial growth factor receptors, or to treat a cancer having such resistance.

Hereinafter, the present disclosure will be described in more detail with reference to the following examples. However, the following examples are presented merely to exemplify the present disclosure and the scope of the present disclosure is not limited thereto.

Example 1: Preparation of N-methyl-N-(2-((2-((4-(4-methylpiperazin-1-yl)phenyl)amino)-7H-pyrrolo[2,3-d]pyrimidine-4-yl)amino)phenyl)methanesulfonamide

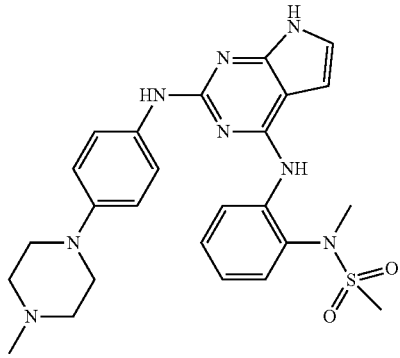

Step 1) Preparation of N-methyl-N-(2-nitrophenyl)methanesulfonamide 20 g (0.14 mol) of 2-fluoronitrobenzene and 23 g (0.21 mol) of N-methylmethanesulfonamide were diluted in 200 mL of acetonitrile, and 92 g (0.28 mol) of cesium carbonate was added thereto and stirred at room temperature for 16 hours. The resulting mixture was diluted with ethyl acetate and washed with distilled water and saturated brine. The resulting separated organic layer was dried with anhydrous sodium sulfate, filtered under reduced pressure, and distilled under reduced pressure to obtain 25 g of the compound of the title (Yield: 78%).

$^1$H-NMR (300 MHz, CDCl$_3$) δ 7.92 (d, 1H), 7.67 (m, 1H), 7.61 (m, 2H), 3.33 (s, 3H), 3.02 (s, 3H).

Step 2) Preparation of N-(2-aminophenyl)-N-methylmethanesulfonamide 30 g (0.54 mol) of iron and 29 g (0.54 mol) of ammonium chloride were diluted in 150 ml of a 40% ethanol aqueous solution, and stirred at 90° C. for 30 minutes. A solution obtained by dissolving 25 g (0.11 mol) of the compound prepared in step 1) in 30 ml of a 40% ethanol aqueous solution was added thereto and stirred at 90° C. for 2 hours. When the reaction was completed, the resulting reaction mixture was filtered through a filter filled with Celite to remove iron, and the resulting filtrate was distilled under reduced pressure. The obtained residue was diluted with a mixed solvent of chloroform and 2-propanol (a volume ratio of 3:1) and washed with a saturated aqueous sodium bicarbonate solution. The resulting separated organic layer was dried with anhydrous sodium sulfate, and thereafter filtered under reduced pressure and distilled under reduced pressure to obtain 20 g of the compound of the title (Yield: 91%).

$^1$H-NMR (300 MHz, DMSO-d$_6$) δ 7.18 (d, 1H), 7.01 (m, 1H), 6.74 (m, 1H), 6.56 (m, 1H), 5.10 (s, 2H), 3.07 (s, 3H), 3.03 (s, 3H).

Step 3)

Preparation of 2,4-dichloro-7-((2-(trimethylsilyl)ethoxy)methyl)-7H-pyrrolo[2,3-d]pyrimidine 25 g (133.0 mmol) of 2,4-dichloro-7H-pyrrolo[2,3-d]pyrimidine was diluted in 200 ml of N,N-dimethylformamide, and 7.98 g (199.5 mmol) of 60% sodium hydride was slowly added thereto at 0° C. and stirred at 0° C. for 30 minutes. 31 ml (172.9 mmol) of 2-(trimethylsilyl)ethoxymethyl chloride was slowly added thereto at 0° C. and stirred at room temperature for 2 hours. After the reaction was completed, the resulting reaction mixture was slowly added dropwise into ice water and stirred. The resulting mixture was diluted with ethyl acetate and washed with distilled water and saturated brine. The resulting separated organic layer was dried with anhydrous sodium sulfate, and thereafter filtered under reduced pressure and distilled under reduced pressure. The resulting residue was separated by column chromatography (hexane:ethyl acetate=4:1 (volume ratio)) to obtain 38.9 g of the compound of the title (Yield: 93%).

$^1$H-NMR (300 MHz, CDCl$_3$) δ 7.37 (d, 1H), 6.65 (d, 1H), 5.60 (s, 2H), 3.54 (m, 2H), 0.91 (m, 2H), 0.01 (s, 9H).

Step 4) Preparation of N-(2-((2-chloro-7-((2-(trimethylsilyl)ethoxy)methyl)-7H-pyrrolo[2,3-d]pyrimidine-4-yl)amino)phenyl)-N-methylmethanesulfonamide 8.8 g (44.0 mmol) of the compound prepared in step 2) and 14 g (44.0 mmol) of the compound prepared in step 3) were diluted with 15 ml of N,N-dimethylformamide, and 14.8 g (131.9 mmol) of tert-butoxypotassium was slowly added thereto at 0° C. and stirred at room temperature for 2 hours. After the reaction was completed, the resulting reaction mixture was slowly added dropwise into ice water and stirred. The resulting mixture was diluted with ethyl acetate and washed with a 1N aqueous hydrochloric acid solution and saturated brine. The resulting separated organic layer was dried with anhydrous sodium sulfate, and thereafter filtered under reduced pressure and distilled under reduced pressure. The resulting residue was separated by column chromatography (hexane: ethyl acetate=2:1 (volume ratio)) to obtain 9.1 g of the compound of the title (Yield: 97%).

$^1$H-NMR (300 MHz, CDCl$_3$) δ 8.49 (d, 1H), 8.38 (s, 1H), 7.46 (t, 1H), 7.34 (m, 1H), 7.22 (m, 1H), 7.14 (d, 1H), 6.49 (d, 1H), 5.58 (s, 2H), 3.55 (t, 2H), 3.30 (s, 3H), 3.02 (s, 3H), 0.95 (t, 2H), 0.01 (s, 9H).

Step 5) Preparation of 1-methyl-4-(4-nitrophenyl)piperazine 10 g (70.9 mmol) of 4-fluoronitrobenzene and 8.6 ml (78.0 mmol) of 1-methyl-4-piperazine were diluted with 80 ml of N,N-dimethylformamide, and 14.7 g (106.4 mmol) of potassium carbonate was added thereto and stirred at 80° C. for 15 hours. When the reaction was completed, the reaction mixture was cooled down to room temperature, and the resulting reaction mixture was slowly added dropwise to ice water and stirred. The resulting solid was washed with distilled water, filtered under reduced pressure, and dried under reduced pressure to obtain 12.5 g of the compound of the title (Yield: 80%).

$^1$H-NMR (300 MHz, DMSO-d$_6$) δ 8.02 (d, 2H), 7.00 (d, 2H), 3.42 (m, 4H), 2.40 (m, 4H), 2.19 (s, 3H).

Step 6) Preparation of 4-(4-methylpiperazin-1-yl)aniline 12.5 g (56.5 mmol) of the compound prepared in step 5) was diluted with 120 ml of ethyl acetate, and thereafter 1.2 g (10 wt %) of palladium/carbon was added thereto at room temperature and stirred under hydrogen gas for 14 hours. After the reaction was completed, the reaction mixture was washed with ethyl acetate and filtered through a Celite-filled filter under reduced pressure, and the resulting filtrate was distilled under reduced pressure to obtain 10 g of the compound of the title (Yield: 93%).

$^1$H-NMR (300 MHz, DMSO-d$_6$) δ 6.65 (d, 2H), 6.47 (d, 2H), 4.55 (brs, 2H), 2.87 (m, 4H), 2.40 (m, 4H), 2.18 (s, 3H).

Step 7)

Preparation of N-methyl-N-(2-((2-((4-(4-methylpiperazin-1-yl)phenyl)amino)-7-((2-(trimethylsilyl)ethoxy)methyl)-7H-pyrrolo[2,3-d]pyrimidine-4-yl)amino)phenyl)methanesulfonamide 150 mg (0.31 mmol) of the compound prepared in step 4) and 54 mg (0.28 mmol) of the compound prepared in step 6) were dissolved in 5 ml of 1,4-dioxane, 15 mg (0.03 mmol) of 2-dicyclohexylphosphino-2',4',6'-triisopropylbiphenyl and 304 mg (0.93 mmol) of cesium carbonate were added thereto and stirred at room temperature for 5 minutes, and thereafter 29 mg (0.03 mmol) of tris(dibenzylideneacetone)dipalladium(0) was added and stirred at 100° C. for 3 hours. When the reaction was completed, the resulting reaction mixture was cooled down to room temperature, filtered with a celite-filled filter, and then the filtrate was diluted in a mixed solvent of chloroform and 2-propanol (3:1 by volume ratio) and washed with water. The resulting separated organic layer was dried with anhydrous sodium sulfate, and thereafter filtered under reduced pressure and distilled under reduced pressure. The resulting residue was separated by column chromatography (dichloromethane:methanol=8:1 (volume ratio)) to obtain 110 mg of the compound of the title (Yield: 56%).

$^1$H-NMR (300 MHz, CDCl$_3$) δ 8.49 (d, 1H), 8.26 (m, 1H), 8.15 (s, 1H), 7.41 (m, 1H), 7.29 (m, 3H), 7.17 (m, 1H), 6.94 (m, 2H), 6.69 (m, 1H), 6.44 (d, 1H), 5.52 (s, 2H), 3.67 (m, 2H), 3.58 (m, 2H), 3.29 (s, 3H), 3.10 (m, 4H), 3.11 (s, 3H), 2.73 (s, 3H), 2.65 (m, 2H), 0.88 (m, 2H), 0.06 (s, 9H).

Step 8)

Preparation of N-methyl-N-(2-((2-((4-(4-methylpiperazin-1-yl)phenyl)amino)-7H-pyrrolo[2,3-d]pyrimidine-4-yl)amino)phenyl)methanesulfonamide 110 mg (0.17 mmol) of the compound prepared in step 7) was diluted with 1.5 ml of dichloromethane, and 2.5 ml of trifluoroacetic acid was added and stirred at room temperature for 2 hours. When the reaction was completed, the resulting reaction mixture was distilled under reduced pressure, and the obtained residue was diluted with 3 ml of tetrahydrofuran, and 9 ml of a 6N sodium hydroxide aqueous solution was added and stirred at room temperature for 4 hours. After the reaction was completed, the resulting reaction mixture was diluted with ethyl acetate and washed with distilled water. The resulting separated organic layer was dried with anhydrous sodium sulfate, and thereafter filtered under reduced pressure and distilled under reduced pressure. The obtained reissue was separated by column chromatography (dichloromethane:methanol=8:1 (volume ratio) to obtain 40 mg of the compound of the title (Yield: 48%).

¹H-NMR (300 MHz, DMSO-d₆) δ 11.24 (s, 1H), 8.62 (s, 1H), 8.41 (d, 1H), 8.16 (s, 1H), 7.59 (m, 3H), 7.36 (m, 1H), 7.18 (m, 1H), 6.91 (d, 1H), 6.82 (d, 2H), 6.22 (d, 1H), 3.20 (s, 3H), 3.09 (s, 3H), 3.04 (m, 4H), 2.41 (m, 4H), 2.23 (s, 3H);

MS (ESI+): m/z=507.2 [M+H]⁺.

Compounds of Examples 2 to Example 30 as represented in Table 1 were prepared in the same or similar manner as in Example 1, except that various derivatives represented by halogen-substituted Cy₂-NO₂ and YH (wherein Cy₂ and Y are as defined herein.) were used instead of 4-fluoronitrobenzene and 1-methyl-4-piperazine used in step 5) of Example 1.

TABLE 1

| Example | Structural formula | Analysis data |
|---|---|---|
| 2 | | ¹H-NMR (300 MHz, DMSO-d₆) δ 11.11 (s, 1H), 8.35 (d, 1H), 8.01 (s, 1H), 7.81 (s, 1H), 7.52 (d, 1H), 7.23-7.18 (m, 2H), 7.09 (t, 1H), 6.83-6.72 (m, 3H), 6.14 (m, 1H), 3.18-3.08 (m, 10H), 2.48 (m, 4H), 2.21 (s, 3H), 2.14 (s, 3H); MS (ESI⁺): m/z = 521.2 [M + H]⁺. |
| 3 | | ¹H-NMR (300 MHz, DMSO-d6) δ 11.23 (s, 1H), 8.37 (d, 1H), 8.28 (s, 1H), 8.10 (s, 1H), 7.56 (m, 1H), 7.45 (m, 1H), 7.25 (m, 1H), 7.13 (m, 1H), 6.85 (d, 1H), 6.73 (d, 1H), 6.69 (d, 1H), 6.20 (s, 1H), 3.27 (m, 4H), 3.19 (s, 3H), 3.13 (m, 4H), 3.10 (s, 3H), 2.24 (s, 3H), MS (ESI+): m/z = 525.2 [M + H]+. |
| 5 | | ¹H-NMR (300 MHz, DMSO-d₆) δ 11.30 (s, 1H), 8.72 (s, 1H), 8.46 (d, 1H), 8.25 (s, 1H), 7.65-7.55 (m, 3H), 7.44 (m, 1H), 7.24 (m, 1H), 7.00-6.95 (m, 2H), 6.31 (d, 1H), 3.26 (s, 3H), 3.16 (s, 3H), 2.85 (m, 4H), 2.56 (m, 4H), 2.36 (s, 3H), 2.25 (s, 3H); MS (ESI⁺): m/z = 521.2 [M + H]⁺. |

TABLE 1-continued

| Example | Structural formula | Analysis data |
|---|---|---|
| 6 | | $^1$H-NMR (300 MHz, DMSO-d$_6$) δ 11.33 (s, 1H), 8.92 (s, 1H), 8.32-8.24 (m, 2H), 8.02 (d, 1H), 7.56 (m, 2H), 7.41 (m, 1H), 7.20 (m, 1H), 7.04-6.96 (m, 2H), 6.27 (m, 1H), 3.25 (s, 3H), 3.09 (s, 3H), 2.90 (m, 4H), 2.50 (m, 4H), 2.23 (s, 3H); MS (ESI$^+$); m/z = 541.2 [M + H]$^+$. |
| 7 | | $^1$H-NMR (300 MHz, DMSO-d$_6$) δ 11.34 (s, 1H), 8.93 (s, 1H), 8.32-8.27 (m, 2H), 7.87 (d, 1H), 7.58 (d, 1H), 7.39 (t, 1H), 7.31 (d, 1H), 7.20 (t, 1H), 6.95 (m, 1H), 6.92 (t, 1H), 6.27 (m, 1H), 3.19 (s, 3H), 3.08 (s, 3H), 2.92 (m, 4H), 2.49 (m, 4H), 2.21 (s, 3H); MS (ESI$^+$): m/z = 525.2 [M + H]$^+$. |
| 8 | | $^1$H-NMR (300 MHz, DMSO-d$_6$) δ 11.33 (s, 1H), 8.91 (s, 1H), 8.32 (d, 1H), 8.26 (s, 1H), 7.72 (d, 1H), 7.58 (d, 1H), 7.30-7.43 (m, 3H), 6.87-6.97 (m, 2H), 6.27 (m, 1H), 3.20 (s, 3H), 3.09 (s, 3H), 2.95 (m, 4H), 2.50 (m, 4H), 2.40 (m, 2H), 1.04 (t, 3H); MS (ESI$^+$): m/z = 539.2 [M + H]$^+$. |
| 9 | | $^1$H-NMR (300 MHz, DMSO-d$_6$) δ 11.3 (brs, 1H), 8.90 (s, 1H), 8.32 (d, 1H), 8.30 (s, 1H), 7.88 (d, 1H), 7.59 (d, 1H), 7.42 (m, 1H), 7.34 (m, 1H), 7.23 (m, 1H), 6.88 (m, 1H), 6.85 (t, 1H), 6.26 (m, 1H), 3.19 (s, 3H), 3.08 (s, 3H), 2.92 (m, 4H), 2.71 (m, 1H), 2.65 (m, 4H), 1.02 (d, 6H); MS (ESI$^+$): m/z = 553.2 [M + H]$^+$. |

TABLE 1-continued

| Example | Structural formula | Analysis data |
|---|---|---|
| 10 | 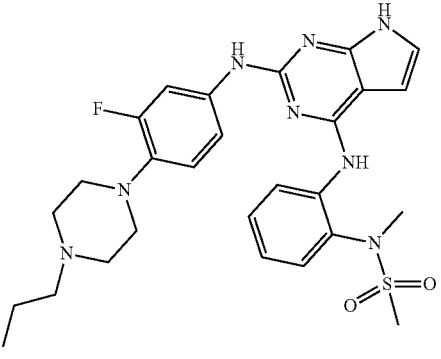 [SMILES: CCCN1CCN(c2ccc(Nc3nc(Nc4ccccc4N(C)S(C)(=O)=O)c4cc[nH]c4n3)cc2F)CC1] | ¹H-NMR (300 MHz, CDCl₃) δ 11.32 (s, 1H), 8.91 (s, 1H), 8.32 (d, 1H), 8.25 (s, 1H), 7.86 (d, 1H), 7.58 (d, 1H), 7.37 (t, 1H), 7.31 (d, 1H), 7.21 (t, 1H), 6.90-6.97 (m, 2H), 6.27 (s, 1H), 3.20 (s, 3H), 3.09 (s, 3H), 3.93 (m, 4H), 2.50 (m, 4H), 2.29 (t, 2H), 1.48 (m, 2H), 0.85 (t, 3H); MS (ESI⁺): m/z = 553.2 [M + H]⁺. |
| 11 | 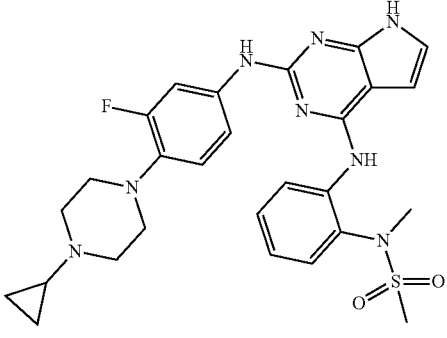 [SMILES: CN(c1ccccc1Nc1nc(Nc2ccc(N3CCN(C4CC4)CC3)c(F)c2)nc2[nH]ccc12)S(C)(=O)=O] | ¹H-NMR (300 MHz, DMSO-d₆) δ 11.33 (s, 1H), 8.91 (s, 1H), 8.33 (d, 1H), 8.26 (s, 1H), 7.80 (m, 1H), 7.60 (m, 1H), 7.35 (m, 1H), 7.30 (m, 1H), 7.20 (m, 1H), 6.97-6.85 (m, 2H), 6.27 (m, 1H), 3.20 (s, 3H), 3.09 (s, 3H), 2.88 (m, 4H), 2.69 (m, 4H), 1.68 (m, 1H), 0.44 (m, 2H), 0.33 (m, 2H); MS (ESI⁺): m/z = 551.2 [M + H]⁺. |
| 12 | 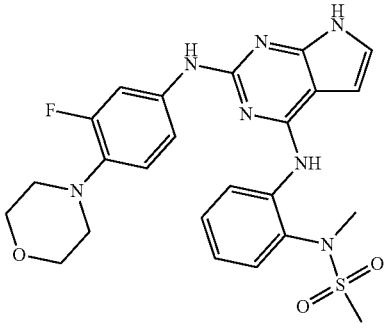 [SMILES: CN(c1ccccc1Nc1nc(Nc2ccc(N3CCOCC3)c(F)c2)nc2[nH]ccc12)S(C)(=O)=O] | ¹H-NMR (300 MHz, CDCl₃) δ 8.97 (brs, 1H), 8.41 (d, 1H), 8.35 (brs, 1H), 7.73 (d, 1H), 7.47-7.44 (m, 2H), 7.33 (m, 1H), 7.23 (t, 1H); 7.09 (m, 1H), 6.92-6.88 (m, 2H), 6.43 (m, 1H), 3.90 (m, 4H), 3.31 (s, 3H), 3.06 (m, 4H), 3.01 (s, 3H); MS (ESI⁺): m/z = 512.2 [M + H]⁺. |
| 13 | 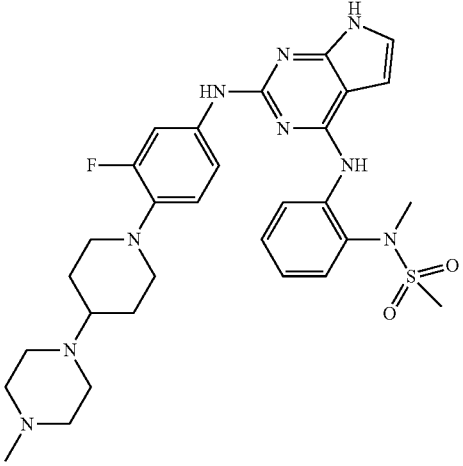 [SMILES: CN1CCN(C2CCN(c3ccc(Nc4nc(Nc5ccccc5N(C)S(C)(=O)=O)c5cc[nH]c5n4)cc3F)CC2)CC1] | ¹H-NMR (300 MHz, DMSO-d₆) δ 11.33 (s, 1H), 8.92 (s, 1H), 8.29 (m, 2H), 8.00 (d, 1H), 7.83 (m, 1H), 7.57 (t, 1H), 7.29 (m, 1H), 7.20 (t, 1H), 6.95 (d, 1H), 6.89 (m, 1H), 6.26 (s, 1H), 3.25 (m, 4H), 3.19 (s, 3H), 3.08 (s, 3H), 2.55 (m, 4H), 2.53 (m, 1H), 2.38 (m, 4H), 2.29 (s, 3H), 1.97 (m, 2H), 1.57 (m, 2H); MS (ESI+): m/z = 608.2 [M + H]⁺. |

TABLE 1-continued

| Example | Structural formula | Analysis data |
|---|---|---|
| 14 | | $^1$H-NMR (300 MHz, DMSO-d$_6$) δ 11.30 (s, 1H), 8.88 (s, 1H), 8.29 (m, 1H), 8.24 (s, 1H), 7.83 (m, 1H), 7.56 (m, 1H), 7.38 (m, 1H), 7.29 (m, 1H), 7.19 (m, 1H), 6.90 (m, 2H), 6.25 (d, 1H), 3.30 (m, 4H), 3.18 (s, 3H), 3.07 (s, 3H), 2.50 (m, 4H), 2.42-2.26 (m, 7H), 1.82 (m, 2H), 1.54 (m, 2H), 0.99 (t, 3H); MS (ESI+): m/z = 622.3 [M + H]$^+$. |
| 15 | | $^1$H-NMR (300 MHz, DMSO-d$_6$) δ 11.33 (s, 1H), 8.90 (s, 1H), 8.31 (m, 1H), 8.25 (s, 1H), 7.85 (dd, 1H), 7.60 (m, 1H), 7.40 (m, 1H), 7.30 (m, 1H), 7.21 (m, 1H), 6.97-6.85 (m, 2H), 6.27 (m, 1H), 3.32 (m, 4H), 3.20 (s, 3H), 3.09 (s, 3H), 2.56 (m, 4H), 2.49 (m, 4H), 2.25 (m, 1H), 1.83 (m, 2H), 1.54 (m, 2H), 0.96 (d, 6H); MS (ESI+): m/z = 636.3 [M + H]$^+$. |
| 16 | | $^1$H-NMR (300 MHz, DMSO-d$_6$) δ 11.31 (s, 1H), 8.89 (s, 1H), 8.29 (d, 1H), 8.24 (s, 1H), 7.83 (d, 1H), 7.58 (d, 1H), 7.38 (t, 1H), 7.31 (d, 1H), 7.21 (t, 1H), 6.94 (m, 1H), 6.85 (m, 1H), 6.25 (d, 1H), 3.25 (m, 4H), 3.19 (s, 3H), 3.08 (s, 3H), 2.55 (m, 4H), 2.53 (m, 4H), 2.38 (m, 3H), 1.89 (m, 2H), 1.56 (m, 2H), 1.45 (m, 2H), 0.84 (t, 3H); MS (ESI+): m/z = 636.3 [M + H]$^+$. |

TABLE 1-continued

| Example | Structural formula | Analysis data |
|---|---|---|
| 17 | | $^1$H-NMR (300 MHz, DMSO-d$_6$) δ 11.31 (s, 1H), 8.87 (s, 1H), 8.28 (d, 1H), 8.23 (s, 1H), 7.84 (d, 1H), 7.78 (d, 1H), 7.55 (t, 1H), 7.38 (d, 1H), 7.18 (t, 1H), 6.92 (m, 1H), 6.88 (m, 1H), 6.24 (d, 1H), 3.28 (m, 4H), 3.17 (s, 3H), 3.06 (s, 3H), 2.48 (m, 4H), 2.24 (m, 2H), 1.78 (m, 2H), 1.53 (m, 3H), 1.21 (m, 2H), 0.89 (m, 1H), 0.37 (m, 2H), 0.25 (m, 2H); MS (ESI+): m/z = 634.3 [M + H]$^+$. |
| 18 | | $^1$H-NMR (300 MHz, DMSO-d$_6$) δ 11.31 (s, 1H), 8.89 (s, 1H), 8.29 (d, 1H), 8.24 (s, 1H), 7.84 (d, 1H), 7.58 (d, 1H), 7.38 (t, 1H), 7.31 (d, 1H), 7.18 (t, 1H), 6.95 (m, 1H), 6.86 (m, 1H), 6.25 (d, 1H), 3.58 (m, 4H), 3.19 (s, 3H), 3.08 (s, 3H), 2.59 (m, 2H), 2.48 (m, 4H), 2.25 (m, 1H), 1.88 (m, 2H), 1.55 (m, 2H), 1.24 (m, 2H); MS (ESI+): m/z = 595.3 [M + H]$^+$. |
| 19 | | $^1$H-NMR (300 MHz, DMSO-d$_6$) δ 11.32 (s, 1H), 8.91 (s, 1H), 8.31 (d, 1H), 8.29 (s, 1H), 7.87 (d, 1H), 7.56 (d, 1H), 7.51 (d, 1H), 7.41 (t, 1H), 7.34 (d, 1H), 7.22 (t, 1H), 6.25 (d, 1H), 4.56 (m, 2H), 4.46 (m, 2H), 3.18 (s, 3H), 3.08 (s, 3H), 3.00 (m, 4H), 2.41 (m, 4H); MS (ESI+): m/z = 567.2 [M + H]$^+$. |

TABLE 1-continued

| Example | Structural formula | Analysis data |
|---|---|---|
| 21 | 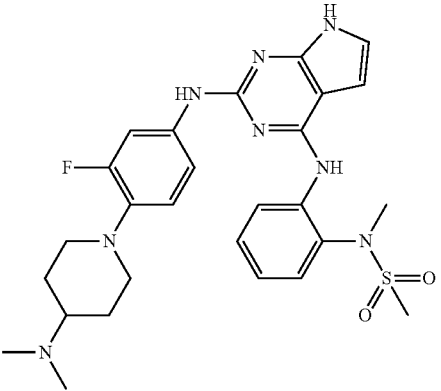 [SMILES: CN(C)C1CCN(c2ccc(Nc3nc(Nc4ccccc4N(C)S(C)(=O)=O)c4cc[nH]c4n3)cc2F)CC1] | $^1$H-NMR (300 MHz, DMSO-d$_6$) δ 11.32 (s, 1H), 8.90 (s, 1H), 8.30 (m, 2H), 7.83 (m, 1H), 7.56 (m, 1H), 7.40-7.16 (m, 3H), 6.94-6.84 (m, 2H), 6.25 (m, 1H), 3.26 (m, 2H), 3.22 (s, 3H), 3.07 (s, 3H), 2.56 (m, 2H), 2.22 (s, 6H), 2.17 (m, 1H), 1.80 (m, 2H), 1.52 (m, 2H); MS (ESI$^+$): m/z = 553.3 [M + H]$^+$. |
| 22 | 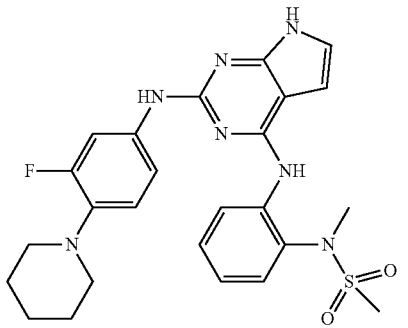 [SMILES: CN(c1ccccc1Nc1nc(Nc2ccc(N3CCCCC3)c(F)c2)nc2[nH]ccc12)S(C)(=O)=O] | $^1$H-NMR (300 MHz, DMSO-d$_6$) δ 8.90 (s, 1H), 8.32 (m, 1H), 8.26 (s, 1H), 7.85 (m, 1H), 7.58 (m, 1H), 7.39 (m, 1H), 7.31 (m, 1H), 7.24 (m, 1H), 6.97-6.87 (m, 2H), 6.27 (m, 1H), 3.21 (s, 3H), 3.10 (s, 3H), 2.88 (m, 4H), 1.65 (m, 4H), 1.52 (m, 2H); MS (ESI$^+$): m/z = 510.2 [M + H]$^+$. |
| 23 | 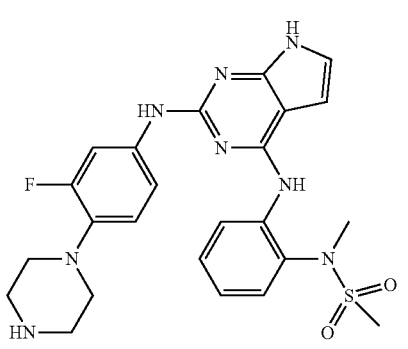 [SMILES: CN(c1ccccc1Nc1nc(Nc2ccc(N3CCNCC3)c(F)c2)nc2[nH]ccc12)S(C)(=O)=O] | $^1$H-NMR (300 MHz, DMSO-d$_6$) δ 11.31 (s, 1H), 8.89 (s, 1H), 8.30 (d, 1H), 8.24 (s, 1H), 7.84 (d, 1H), 7.56 (m, 1H), 7.38 (t, 1H), 7.30 (m, 1H), 7.21 (t, 1H), 6.95 (m, 1H), 6.84 (t, 1H), 6.26 (m, 1H), 3.19 (s, 3H), 3.08 (s, 3H), 2.85 (m, 8H); MS (ESI$^+$): m/z = 511.2 [M + H]$^+$. |
| 24 | 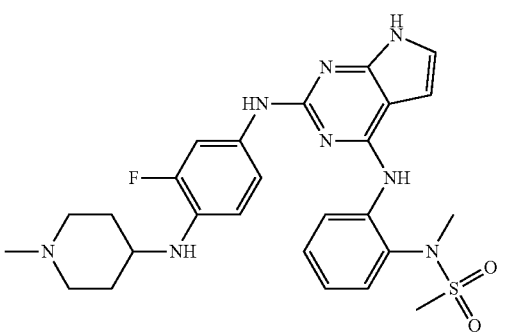 [SMILES: CN1CCC(Nc2ccc(Nc3nc(Nc4ccccc4N(C)S(C)(=O)=O)c4cc[nH]c4n3)cc2F)CC1] | $^1$H-NMR (300 MHz, DMSO-d$_6$) δ 11.25 (s, 1H), 8.66 (s, 1H), 8.37 (d, 1H), 8.19 (s, 1H), 7.74 (d, 1H), 7.57 (d, 1H), 7.37 (t, 1H), 7.19-7.17 (m, 2H), 6.92 (s, 1H), 6.66 (t, 1H), 6.23 (m, 1H), 4.49 (d, 1H), 3.20 (s, 3H), 3.09 (s, 3H), 2.74 (m, 2H), 2.16 (s, 3H), 1.98 (m, 3H), 1.85 (m, 2H), 1.42 (m, 2H); MS (ESI$^+$): m/z = 539.2 [M + H]$^+$. |

TABLE 1-continued

| Example | Structural formula | Analysis data |
|---|---|---|
| 25 | 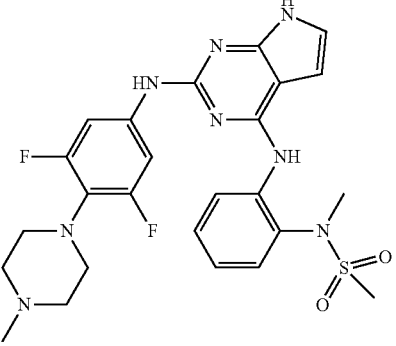 | ¹H-NMR (300 MHz, DMSO-d$_6$) δ 11.37 (s, 1H), 9.12 (s, 1H), 8.34 (s, 1H), 8.17 (d, 1H), 7.57 (d, 1H), 7.51 (d, 1H), 7.38 (d, 1H), 7.35 (t, 1H), 7.23 (t, 1H), 6.97 (d, 1H), 6.28 (d, 1H), 3.17 (s, 3H), 3.04 (s, 3H), 2.99 (m, 4H), 2.41 (m, 4H), 2.22 (s, 3H); MS (ESI⁺): m/z = 543.6 [M + H]⁺. |
| 26 | 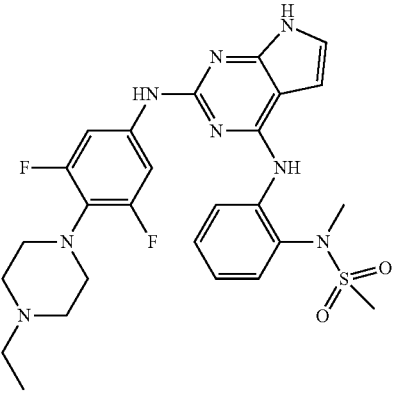 [SMILES: CCN1CCN(c2c(F)cc(Nc3nc(Nc4ccccc4N(C)S(C)(=O)=O)c4cc[nH]c4n3)cc2F)CC1] | ¹H-NMR (300 MHz, DMSO-d$_6$) δ 11.37 (s, 1H), 9.12 (s, 1H), 8.34 (s, 1H), 8.15 (m, 1H), 7.58 (m, 1H), 7.51 (m, 2H), 7.38 (m, 1H), 7.23 (m, 1H), 6.97 (m, 1H), 6.29 (m, 1H), 3.16 (s, 3H), 3.05 (s, 3H), 3.00 (m, 4H), 2.43 (m, 4H), 2.33 (q, 2H), 0.99 (t, 3H); MS (ESI⁺): m/z = 557.6 [M + H]⁺. |
| 27 | 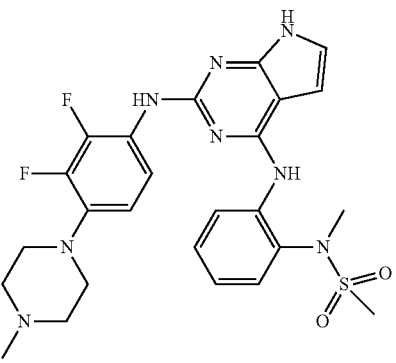 [SMILES: CN1CCN(c2ccc(Nc3nc(Nc4ccccc4N(C)S(C)(=O)=O)c4cc[nH]c4n3)c(F)c2F)CC1] | ¹H-NMR (300 MHz, DMSO-d$_6$) δ 11.29 (s, 1H), 8.36 (s, 1H), 8.31 (d, 1H), 8.18 (s, 1H), 7.55 (d, 1H), 7.36 (m, 1H), 7.33 (m, 1H), 7.14 (m, 1H), 6.92 (d, 1H), 6.77 (t, 1H), 6.23 (s, 1H), 3.38 (m, 4H), 3.20 (s, 3H), 3.15 (s, 3H), 3.09 (m, 4H), 2.23 (s, 3H); MS (ESI+): m/z = 543.2 [M + H]⁺. |
| 28 | 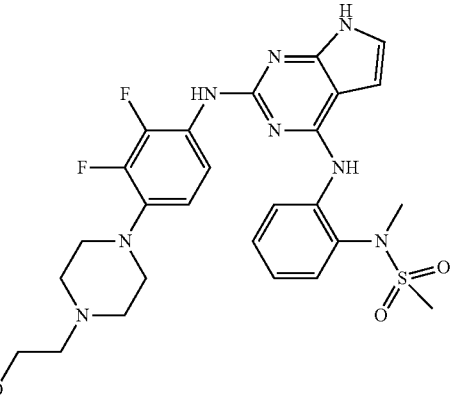 | ¹H-NMR (300 MHz, DMSO-d$_6$) δ 11.29 (s, 1H), 8.36 (s, 1H), 8.31 (d, 1H), 8.18 (s, 1H), 7.55 (d, 1H), 7.36 (m, 1H), 7.27 (m, 1H), 7.14 (m, 1H), 6.94 (d, 1H), 6.78 (t, 1H), 6.23 (s, 1H), 4.44 (t, 1H), 3.55 (m, 2H), 3.19 (s, 3H), 3.09 (s, 3H), 3.02 (m, 4H), 2.59 (m, 4H), 2.43 (m, 2H); MS (ESI+): m/z = 573.2 [M + H]⁺. |

TABLE 1-continued

| Example | Structural formula | Analysis data |
|---|---|---|
| 29 | | $^1$H-NMR (300 MHz, DMSO-$d_6$) δ 11.37 (s, 1H), 8.73 (s, 1H), 8.49 (d, 1H), 8.24 (s, 1H), 8.13 (d, 1H), 7.92 (s, 1H), 7.56 (d, 1H), 7.37 (t, 1H), 7.29 (m, 1H), 7.14 (t, 1H), 6.25 (m, 1H), 5.74 (s, 1H), 3.18 (s, 3H), 3.15-3.08 (m, 7H), 2.43 (m, 4H), 2.23 (s, 3H); MS (ESI$^+$): m/z = 508.2 [M + H]$^+$. |
| 30 | | $^1$H-NMR (300 MHz, DMSO-$d_6$) δ 11.24 (s, 1H), 8.63 (s, 1H), 8.45 (s, 1H), 8.34 (s, 1H), 8.18 (s, 1H), 7.92 (m, 1H), 7.55 (m, 1H), 7.35 (m, 1H), 7.17 (m, 1H), 6.91 (m, 1H), 6.74 (m, 1H), 6.21 (m, 1H), 3.33 (m, 4H), 3.19 (s, 3H), 3.08 (s, 3H), 2.40 (m, 4H), 2.21 (s, 3H); MS (ESI$^+$): m/z = 508.2 [M + H]$^+$. |

Example 4: Preparation of N-(2-((2-((3-hydroxy-4-(4-methylpiperazin-1-yl)phenyl)amino)-7H-pyrrolo[2,3-d]pyrimidine-4-yl)amino)phenyl)-N-methyl-methanesulfonamide

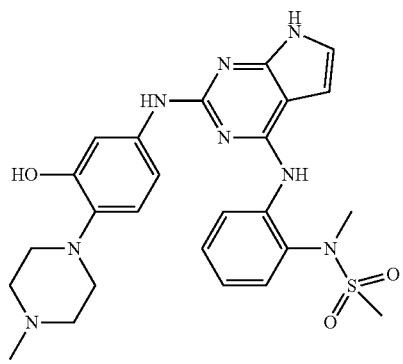 [SMILES: CN1CCN(c2ccc(Nc3nc(Nc4ccccc4N(C)S(C)(=O)=O)c4cc[nH]c4n3)cc2O)CC1]

Step 1) Preparation of 2,4-dichloro-7-tosyl-7H-pyrrolo[2,3-d]pyrimidine 20 g (106 mmol) of 2,4-dichloro-7H-pyrrolo[2,3-d]pyrimidine was diluted with 300 ml of dichloromethane, 22 ml (159 mmol) of triethylamine and 1.3 g (10.6 mmol) of 4-(dimethylamino)pyridine were added thereto and cooled down to 0° C., and 30 g (159 mmol) of p-toluenesulfonyl chloride was slowly added and then stirred at room temperature for 16 hours. After the reaction was completed, the resulting reaction mixture was diluted with dichloromethane and washed with saturated brine. The resulting separated organic layer was washed with dichloromethane in a Celite-filled filter and filtered under reduced pressure, and the filtrate was dried with anhydrous sodium sulfate, and thereafter filtered under reduced pressure and distilled under reduced pressure. The resulting residue was stirred in a mixed solvent of dichloromethane and hexane, and thereafter the resulting solid was filtered to obtain 32 g of the compound of the title (Yield: 85%).

$^1$H-NMR (300 MHz, CDCl$_3$) δ 8.11 (d, 2H), 7.76 (d, 1H), 7.34 (d, 2H), 6.67 (d, 1H), 2.44 (s, 3H).

Step 2) Preparation of N-(2-((2-chloro-7-tosyl-7H-pyrrolo[2,3-d]pyrimidine-4-yl)amino)phenyl)-N-methylmethanesulfonamide 2.74 g (8.00 mmol) of the compound prepared in step 1) and 1.46 g (7.28 mmol) of the compound prepared in step 2) of Example 1 were dissolved in 30 ml of n-butanol, and thereafter 3.81 ml (21.8 mmol) of N,N-diisopropylethylamine was added thereto, sealed, and stirred at 110° C. for 48 hours. When the reaction was completed, the resulting reaction mixture was cooled down to room temperature, diluted with ethyl acetate, and thereafter washed with water. The resulting separated organic layer was dried with anhydrous sodium sulfate, and thereafter filtered under reduced pressure and distilled under reduced pressure. The resulting residue was separated by column chromatography (hexane: ethyl acetate=1:1 (volume ratio)) to obtain 1.3 g of the compound of the title (Yield: 35%).

$^1$H-NMR (300 MHz, CDCl$_3$) δ 8.41 (s, 1H), 8.31 (d, 1H), 8.11 (d, 2H), 7.51-7.26 (m, 5H), 7.19 (m, 1H), 6.48 (d, 1H), 3.25 (s, 3H), 2.97 (s, 3H), 2.41 (s, 3H).

Step 3) Preparation of 1-chloro-2-(methoxymethoxy)-4-nitrobenzene 4.12 g (23.5 mmol) of 2-chloro-5-nitrophenol was diluted with 60 ml of N,N-dimethylformamide, and 1.68 g (42.0 mmol) of a 60% sodium hydride was slowly added thereto at 15° C. and stirred for 30 minutes. 2.18 ml (28.2 mmol) of chloromethyl methyl ether was slowly added thereto at 15° C., and stirred at room temperature for 16 hours. After the reaction was completed, the resulting reaction mixture was diluted with ethyl acetate and washed with distilled water. The resulting separated organic layer was dried with anhydrous sodium sulfate, and thereafter filtered under reduced pressure and distilled under reduced pressure. The resulting residue was separated by column chromatography (hexane:ethyl acetate=15:1 (volume ratio)) to obtain 4.1 g of the compound of the title (Yield: 80%).

$^1$H-NMR (300 MHz, DMSO-d6) δ 8.04 (d, 1H), 7.89 (dd, 1H), 7.77 (dd, 1H) 5.47 (s, 2H), 3.44 (s, 3H).

Step 4) Preparation of 1-(2-(methoxymethoxy)-4-nitrophenyl)-4-methylpiperazin 4.1 g (18.8 mmol) of the compound prepared in step 3) and 3.6 g (35.9 mmol) of 1-methyl piperazine were dissolved in 80 ml of 1,4-dioxane, and thereafter 2.18 g (3.76 mmol) of 4,5-bis(diphenylphosphino)-9,9-dimethylxantane and 18.4 g (56.4 mmol) of cesium carbonate were added thereto and stirred at room temperature for 5 minutes. 422 mg (1.88 mmol) of palladium(II) acetate was added and stirred at 100° C. for 8 hours. When the reaction was completed, the resulting reaction mixture was cooled down to room temperature and filtered with a Celite-filled filter, and thereafter, the filtrate was distilled in dichloromethane and washed with water. The resulting separated organic layer was dried with anhydrous sodium sulfate, and thereafter filtered under reduced pressure and distilled under reduced pressure. The resulting residue was separated by column chromatography (dichloromethane:methanol=10:1 (volume ratio)) to obtain 2.8 g of the compound of the title (Yield: 53%).

$^1$H-NMR (300 MHz, DMSO-d6) δ 7.91 (m, 2H), 7.06 (d, 1H), 5.34 (s, 2H), 3.47 (s, 3H), 3.25 (m, 4H), 2.48 (m, 4H), 2.24 (s, 3H).

Step 5) Preparation of 3-(methoxymethoxy)-4-(4-methylpiperazin-1-yl)aniline 1.2 g (Yield: 48%) of the compound of the title was obtained through the same process as in step 6) of Example 1, except that the compound prepared in step 4), instead of 1-methyl-4-(4-nitrophenyl)piperazine, was used in step 6) of Example 1.

$^1$H-NMR (300 MHz, CDCl$_3$) δ 6.64 (d, 1H), 6.30 (d, 1H), 6.14 (dd, 1H) 5.08 (s, 2H), 4.73 (s, 2H), 3.38 (s, 3H), 2.80 (m, 4H), 2.41 (m, 4H), 2.19 (s, 3H).

Step 6) Preparation of N-(2-((2-((3-(methoxymethoxy)-4-(4-methylpiperazin-1-yl)phenyl)amino)-7-tosyl-7H-pyrrolo[2,3-d]pyrimidine-4-yl)amino)phenyl)-N-methylmethanesulfonamide 572 mg (1.13 mmol) of the compound prepared in step 2) and 286 mg (1.13 mmol) of the compound prepared in step 5) were dissolved in 17 ml of tert-butanol, and 108 mg (0.23 mmol) of 2-dicyclohexylphosphino-2',4',6'-triisopropylbiphenyl and 313 mg (2.26 mmol) of potassium carbonate were added thereto and stirred at room temperature for 5 minutes, and thereafter 100 mg (0.11 mmol) of tris(dibenzylideneacetone)dipalladium(0) was added and stirred at 90° C. for 16 hours. When the reaction was completed, the resulting reaction mixture was cooled down to room temperature, diluted with dichloromethane, and thereafter washed with water. The resulting separated organic layer was dried with anhydrous sodium sulfate, and thereafter filtered under reduced pressure and distilled under reduced pressure. The resulting residue was separated by column chromatography (dichloromethane:methanol=9:1 (volume ratio)) to obtain 630 mg of the compound of the title (Yield: 77%).

$^1$H-NMR (300 MHz, DMSO-d6) δ 9.03 (s, 1H), 8.63 (s, 1H), 7.98 (m, 3H), 7.57 (m, 2H), 7.41-7.33 (m, 5H), 7.25 (m, 1H), 6.83 (m, 1H), 6.63 (m, 1H), 5.17 (s, 2H), 3.43 (s, 3H), 3.15 (s, 3H), 3.00 (s, 3H), 2.99 (m, 4H), 2.49 (m, 4H), 2.31 (s, 3H), 2.22 (s, 3H).

Step 7) Preparation of N-(2-((2-((3-(methoxymethoxy)-4-(4-methylpiperazin-1-yl)phenyl)amino)-7H-pyrrolo[2,3-d]pyrimidine-4-yl)amino)phenyl)-N-methylmethanesulfonamide 300 mg (0.42 mmol) of the compound prepared in step 6) was diluted with 4 ml of a mixed solvent of tetrahydrofuran and methanol (1:1 (volume ratio)), and 1 ml of a 4N sodium hydride aqueous solution was added, and thereafter stirred at room temperature for 16 hours. After the reaction was completed, the resulting reaction mixture was diluted with dichloromethane and then washed with distilled water. The resulting separated organic layer was dried with anhydrous sodium sulfate, and thereafter filtered under reduced pressure and distilled under reduced pressure. The obtained residue was separated by column chromatography (dichloromethane:methanol=15:1 (volume ratio) to obtain 218 mg of the compound of the title (Yield: 92%).

$^1$H-NMR (300 MHz, DMSO-d6) δ 11.24 (s, 1H), 8.70 (s, 1H), 8.41 (m, 1H), 8.17 (s, 1H), 7.58 (m, 1H), 7.60-7.34 (m, 3H), 7.19 (m, 1H), 6.94 (m, 1H), 6.92 (d, 1H), 6.23 (m, 1H), 5.11 (s, 2H), 3.42 (s, 3H), 3.20 (s, 3H), 3.09 (s, 3H), 2.93 (m, 4H), 2.49 (m, 4H), 2.22 (s, 3H).

Step 8) Preparation of N-(2-((2-((3-hydroxy-4-(4-methylpiperazin-1-yl)phenyl)amino)-7H-pyrrolo[2,3-d]pyrimidine-4-yl)amino)phenyl)-N-methylmethanesulfonamide 120 mg (0.21 mmol) of the compound prepared in step 7) was diluted with 2 ml of dichloromethane, and 1 ml of trifluoroacetic acid was added thereto and then stirred at room temperature for 4 hours. When the reaction was completed, the resulting reaction mixture was filtered under reduced pressure and distilled under reduced pressure. The obtained residue was separated by column chromatography (dichloromethane:methanol=10:1 (volume ratio)) to obtain 22 mg of the compound of the title (Yield: 20%).

$^1$H-NMR (300 MHz, DMSO-d6) δ 11.20 (s, 1H), 8.60 (s, 1H), 8.43 (d, 1H), 8.12 (s, 1H), 7.56 (m, 1H), 7.33 (m, 1H), 7.22 (m, 1H), 7.15 (m, 2H), 6.91 (m, 1H), 6.79 (d, 1H), 6.20 (m, 1H), 3.19 (s, 3H), 3.08 (s, 3H), 2.83 (m, 4H), 2.49 (m, 4H), 2.21 (s, 3H);

MS (ESP): m/z=523.2 [m+H]$^+$.

Example 20

Preparation of N-(2-((2-((3-fluoro-4-(1-methylpiperidin-4-yl)phenyl)amino)-7H-pyrrolo[2,3-d]pyrimidine-4-yl)amino)phenyl)-N-methylmethanesulfonamide

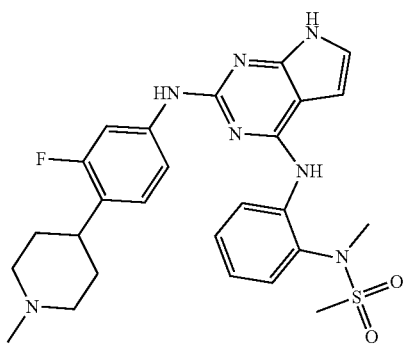 [SMILES: CN1CCC(c2ccc(Nc3nc(Nc4ccccc4N(C)S(C)(=O)=O)c4cc[nH]c4n3)cc2F)CC1]

Step 1

Preparation of 4-(2-fluoro-4-nitrophenyl)-1-methyl-1,2,3,6-tetrahydropyridine 1 g (4.31 mmol) of 5-bromo-2-nitroanisole and 961 mg (4.53 mmol) of 1-methyl-1,2,3,6-tetrahydropyridin-4-boronic acid pinacol ester were diluted with N,N-dimethylformamide, and 1.8 g (12.9 mmol) of potassium carbonate and 190 mg (0.26 mmol) of [1,1'-bis(diphenylphosphino)ferrocene]dichloropalladium(II) were added, and thereafter stirred at 90° C. for 1.5 hours. When the reaction was completed, the resulting reaction mixture was cooled down to room temperature, diluted with ethyl acetate, and thereafter washed with distilled water. The resulting separated organic layer was dried with anhydrous sodium sulfate, and thereafter filtered under reduced pressure and distilled under reduced pressure. The obtained residue was separated by column chromatography (hexane:ethyl acetate=4:1 (volume ratio) to obtain 875 mg of the compound of the title (Yield: 86%).

Step 2

Preparation of N-(2-((2-((3-fluoro-4-(1-methylpiperidin-4-yl)phenyl)amino)-7H-pyrrolo[2,3-d]pyrimidine-4-yl)amino)phenyl)-N-methylmethanesulfonamide 35 mg of the compound of the title (Final step yield: 37%) was obtained through the same process as in Example 1, except that the compound prepared in step 1) was used in step 6), instead of performing step 5) of Example 1.

$^1$H-NMR (300 MHz, CDCl$_3$) δ 8.51-8.49 (m, 2H), 8.16 (s, 1H), 7.72 (d, 1H), 7.43 (t, 1H), 7.31 (t, 1H), 7.19-7.12 (m, 3H), 6.87 (m, 2H), 6.43 (m, 1H), 3.31 (s, 3H), 3.02 (s, 3H), 2.98 (m, 2H), 2.81 (m, 1H), 2.35 (s, 3H), 2.19 (m, 2H), 1.82 (m, 4H);

MS (ESI+): m/z=524.2 [M+H]$^+$.

Example 31

Preparation of N-(2-((2-((3-fluoro-4-(9-methyl-3,9-diazaspiro[5.5]undecan-3-yl)phenyl)amino)-7H-pyrrolo[2,3-d]pyrimidine-4-yl)amino)phenyl)-N-methylmethanesulfonamide

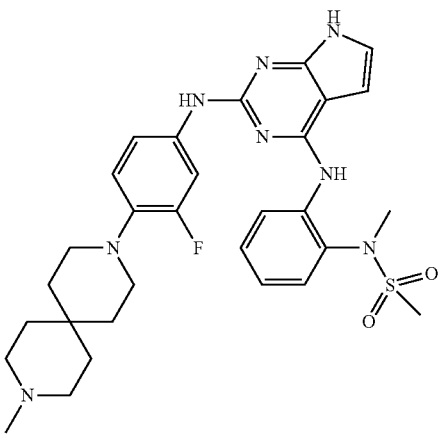 [SMILES: CN1CCC2(CC1)CCN(c1ccc(Nc3nc(Nc4ccccc4N(C)S(C)(=O)=O)c4cc[nH]c4n3)cc1F)CC2]

Step 1

Preparation of tert-butyl 9-methyl-3,9-diazaspiro[5.5]undecan-3-carboxylate 2 g (6.88 mmol) of tert-butyl 3,9-diazaspiro[5.5]undecan-3-carboxylate was diluted with 20 ml of methanol 20 ml, and 2 ml of formaldehyde was added thereto and then stirred at room temperature for 1 hour 390 mg (10.3 mmol) of sodium borohydride was slowly added at 0° C. and then stirred at room temperature for 2 hours After the reaction was completed, the reaction mixture was diluted with ethyl acetate and then washed with sodium bicarbonate and distilled water. The resulting separated organic layer was dried with anhydrous sodium sulfate and then filtered under reduced pressure and distilled under reduced pressure to obtain 1.45 g of the compound of the title (Yield: 78%).

$^1$H-NMR (300 MHz, CDCl$_3$) δ 3.39 (m, 4H), 2.65 (m, 4H), 2.47 (s, 3H), 1.67 (m, 4H), 1.46 (s, 9H), 1.44 (m, 4H).

Step 2) Preparation of 3-methyl-3,9-diazaspiro[5.5]undecan 1.45 g (5.40 mmol) of the compound prepared in step 1) was diluted with 10 ml of dichloromethane, and thereafter 5 ml of trifluoroacetic acid was added and then stirred at room temperature for 2 hours. After the reaction was completed, the reaction mixture was distilled under reduced pressure to obtain 920 mg of the compound of the title (Yield: 99%).

Step 3

Preparation of N-(2-((2-((3-fluoro-4-(9-methyl-3,9-diazaspiro[5.5]undecan-3-yl)phenyl)amino)-7H-pyrrolo[2,3-d]pyrimidine-4-yl)amino)phenyl)-N-methylmethanesulfonamide 36 mg of the compound of the title (Final step yield: 43%) was obtained through the same process as in Example 1, except that the compound prepared in step 2) was used instead of 1-methyl-4-piperazine prepared in step 5) of Example 1.

¹H-NMR (300 MHz, DMSO-d6) δ 11.31 (s, 1H), 8.89 (s, 1H), 8.32 (m, 1H), 8.25 (s, 1H), 7.83 (m, 1H), 7.59 (m, 1H), 7.41 (m, 1H), 7.38 (m, 1H), 7.23 (m, 1H), 6.96 (m, 2H), 6.27 (d, 1H), 3.20 (s, 3H), 3.10 (s, 3H), 2.88 (m, 4H), 2.29 (m, 4H), 2.16 (s, 3H), 1.56 (m, 4H), 1.49 (m, 4H);

MS (ESI+): m/z=592.3 [M+H]⁺.

The compounds of Examples 32 to 41 as represented in Table 2 were prepared in the same or similar manner as the method of Example 31, except that various derivatives represented by spiro-substituted Y—H (wherein Y is as defined herein) were used instead of tert-butyl 3,9-diazaspiro[5.5]undecan-3-carboxylate used in step 1) of Example 31.

TABLE 2

| Example | Structural formula | Analysis data |
|---|---|---|
| 32 | | ¹H-NMR (300 MHz, DMSO-d₆) δ 11.3 (s, 1H), 8.87 (s, 1H), 8.31 (d, 1H), 8.23 (s, 1H), 7.83 (d, 1H), 7.57 (d, 1H), 7.38 (t, 1H), 7.31 (d, 1H), 7.21 (t, 1H), 6.93 (m, 1H), 6.87 (m, 1H), 6.24 (d, 1H), 3.18 (s, 3H), 3.07 (s, 3H), 2.85 (m, 4H), 2.37 (m, 4H), 1.50 (m, 10H), 0.99 (t, 3H); MS (ESI⁺): m/z = 607.3 [M + H]⁺. |
| 33 | | ¹H-NMR (300 MHz, DMSO-d₆) δ 8.85 (s, 1H), 8.27 (s, 1H), 8.21 (s, 1H), 7.80 (m, 1H), 7.54 (m, 1H), 7.34 (m, 1H), 7.27 (m, 1H), 7.17 (m, 1H), 6.89 (m, 2H), 6.22 (m, 1H), 3.16 (s, 3H), 3.05 (s, 3H), 2.82 (m, 4H), 2.42 (m, 4H), 2.17 (s, 3H), 1.59 (m, 6H); MS (ESI⁺): m/z = 579.3 [M + H]⁺. |
| 34 | | ¹H-NMR (300 MHz, DMSO-d₆) δ 11.3 (s, 1H), 8.88 (s, 1H), 8.30 (m, 1H), 8.24 (s, 1H), 7.83 (m, 1H), 7.56 (m, 1H), 7.36 (m, 1H), 7.29 (m, 1H), 7.19 (m, 1H), 6.95-6.84 (m, 2H), 6.25 (m, 1H), 3.18 (s, 3H), 3.07 (s, 3H), 2.92 (s, 4H), 2.81 (m, 4H), 2.21 (s, 3H), 1.77 (m, 4H); MS (ESI⁺): m/z = 565.2 [M + H]⁺. |

TABLE 2-continued

| Example | Structural formula | Analysis data |
|---|---|---|
| 35 | | $^1$H-NMR (300 MHz, DMSO-d$_6$) δ 11.27 (s, 1H), 8.73 (s, 1H), 8.37 (d, 1H), 8.19 (s, 1H), 7.76 (d, 1H), 7.57 (d, 1H), 7.40 (t, 1H), 7.15-7.35 (m, 2H), 6.93 (d, 1H), 6.63 (t, 1H), 6.23 (m, 1H), 3.29 (m, 2H), 3.20 (s, 3H), 3.09 (s, 3H), 3.07 (m, 2H), 2.30 (m, 4H), 2.15 (s, 3H), 1.72 (t, 2H), 1.54 (m, 4H); MS (ESI$^+$): m/z = 579.2 [M + H]$^+$. |
| 36 | | $^1$H-NMR (300 MHz, DMSO-d$_6$) δ 9.11 (s, 1H), 8.52 (d, 1H), 8.11 (s, 1H), 7.57 (d, 1H), 7.43 (t, 1H), 7.32 (m, 1H), 7.13 (t, 1H), 7.00 (d, 1H), 6.74-6.76 (m, 2H), 6.37-.43 (m, 2H), 3.97 (s, 4H), 3.40 (s, , 4H), 3.30 (s, 3H), 3.02 (s, 3H), 2.34 (s, 3H); MS (ESI$^+$): m/z = 537.2 [M + H]$^+$. |
| 37 | | $^1$H-NMR (300 MHz, DMSO-d$_6$) δ 11.27 (s, 1H), 8.74 (s, 1H), 8.36 (d, 1H), 8.20 (s, 1H), 7.75 (d, 1H), 7.58 (d, 1H), 7.39 (t, 1H), 7.17-7.27 (m, 2H), 6.94 (d, 1H), 6.43 (t, 1H), 6.25 (m, 1H), 3.55 (m, 4H), 3.20 (s, 3H), 3.09 (s, 3H), 2.27 (m, 4H), 2.13 (s, 3H), 1.75 (m, 4H); MS (ESI$^+$): m/z = 565.2 [M + H]$^+$. |
| 38 | | $^1$H-NMR (300 MHz, DMSO-d$_6$) δ 9.58 (s, 1H), 8.53 (d, 1H), 8.11 (s, 1H), 7.55 (d, 1H), 7.41 (t, 1H), 7.31 (m, 1H), 7.12 (t, 1H), 7.00 (m, 1H), 6.85 (s, 1H), 6.65 (s, 1H), 6.35-6.64 (m, 2H), 3.91 (m, 2H), 3.83 (m, 2H), 3.29 (s, 3H), 3.01 (s, 3H), 2.80 (s, 2H), 2.59 (t, 2H), 2.39 (s, 3H), 2.15 (t, 2H); MS (ESI$^+$): m/z = 551.2 [M + H]$^+$. |

TABLE 2-continued

| Example | Structural formula | Analysis data |
|---|---|---|
| 39 | | $^1$H-NMR (300 MHz, DMSO-d$_6$) δ 11.30 (s, 1H), 8.90 (s, 1H), 8.27 (d, 1H), 8.24 (s, 1H), 7.82 (d, 1H), 7.56 (d, 1H), 7.36 (t, 1H), 7.31 (d, 1H), 7.20 (t, 1H), 6.85 (s, 1H), 6.65 (s, 1H), 6.25 (d, 1H), 3.58 (m, 4H), 3.19 (s, 3H), 3.08 (s, 3H), 2.59 (m, 4H), 2.48 (m, 4H), 2.25 (m, 4H); MS (ESI+): m/z = 580.2 [M + H]$^+$. |
| 40 | | $^1$H-NMR (300 MHz, DMSO-d$_6$) δ 11.32 (s, 1H), 8.91 (s, 1H), 8.30 (d, 1H), 8.28 (s, 1H), 7.87 (d, 1H), 7.54 (d, 1H), 7.40 (t, 1H), 7.36 (d, 1H), 7.21 (t, 1H), 6.96 (m, 1H), 6.87 (m, 1H), 6.25 (d, 1H), 4.50 (m, 2H), 4.42 (m, 2H), 3.16 (s, 3H), 3.09 (s, 3H), 3.00 (m, 4H), 2.40 (m, 4H); MS (ESI+): m/z = 552.2 [M + H]$^+$. |
| 41 | | $^1$H-NMR (300 MHz, DMSO-d$_6$) δ 8.84 (s, 1H), 8.36 (m, 1H), 8.25 (s, 1H), 7.83 (m, 1H), 7.60 (m, 1H), 7.41 (m, 1H), 7.31 (m, 1H), 7.22 (m, 1H), 6.97 (m, 1H), 6.75 (dd, 1H), 6.27 (d, 1H), 3.27 (s, 3H), 3.28 (m, 2H), 3.11 (s, 3H), 2.94 (m, 2H), 2.79 (m, 2H), 2.59 (m, 2H), 2.36 (m, 2H), 2.24 (s, 3H); MS (ESI$^+$): m/z = 551.3 [M + H]$^+$. |

The compounds of Examples 42 to 56 as represented in Table 3 were prepared in the same or similar manner as the method of Example 1, except that various sulfonamides substituted with $R_1$ and $R_2$, represented by $R_2S(O)_2NH(R_1)$ ($R_1$ and $R_2$ are as defined herein), were used instead of N-methylmethanesulfonamide used in step 1) of Example 1, and various derivatives represented by halogen-substituted Cy$_2$-NO$_2$ and Y—H (Cy$_2$ and Y are as defined herein) were used instead of 4-fluoronitrobenzene and 1-methyl-4-piperazine used in step 5).

TABLE 3

| Example | Structural formula | Analysis data |
|---|---|---|
| 42 | | $^1$H-NMR (300 MHz, DMSO-d$_6$) δ 11.26 (s, 1H), 9.16 (br, 1H), 8.82 (s, 1H), 8.69 (s, 1H), 7.88 (d, 1H), 7.79 (d, 1H), 7.36 (d, 1H), 7.13-7.27 (m, 3H), 6.91 (m, 1H), 6.83 (t, 1H), 6.32 (s, 1H), 2.88 (m, 4H), 2.83 (s, 3H), 2.43 (m, 4H), 2.42 (s, 3H); MS (ESI$^+$): m/z = 510.2 [M + H]$^+$. |
| 43 | | $^1$H-NMR (300 MHz, DMSO-d$_6$) δ 11.3 (s, 1H), 8.99 (s, 1H), 8.51 (d, 1H), 8.00 (s, 1H), 7.86 (m, 1H), 7.58 (m, 1H), 7.45 (m, 1H), 7.35 (m, 1H), 7.20 (m, 1H), 6.98 (s, 1H), 6.95 (m, 1H), 6.18 (s, 1H), 3.80 (m, 2H), 3.15 (s, 3H), 2.94 (m, 4H), 2.50 (m, 4H), 2.23 (s, 3H), 0.98 (t, 3H); MS (ESI$^+$): m/z = 539.2 [M + H]$^+$. |
| 44 | | $^1$H-NMR (300 MHz, DMSO-d$_6$) δ 11.43 (s, 1H), 9.02 (s, 1H), 8.55 (d, 1H), 7.88 (d, 1H), 7.84 (s, 1H), 7.45 (m, 2H), 7.33 (d, 1H), 7.18 (t, 1H), 7.00 (s, 1H), 6.91 (t, 1H), 6.17 (s, 1H), 4.45 (m, 1H), 3.32 (m, 4H), 3.20 (s, 3H), 2.96 (m, 4H), 2.26 (s, 3H), 1.19 (d, 3H), 0.96 (t, 3H); MS (ESI$^+$): m/z = 553.3 [M + H]$^+$. |
| 45 | | $^1$H-NMR (300 MHz, DMSO-d$_6$) δ 11.38 (s, 1H), 8.97 (s, 1H), 8.43 (d, 1H), 7.87 (d, 1H), 7.80 (s, 1H), 7.62 (d, 1H), 7.42-7.32 (m, 2H), 7.20 (t, 1H), 6.97-6.89 (m, 2H), 6.13 (s, 1H), 3.23 (s, 3H), 2.94 (m, 4H), 2.50 (m, 4H), 2.27 (m, 1H), 2.23 (s, 3H), 0.89 (m, 2H), 0.54-0.25 (m, 2H); MS (ESI$^+$): m/z = 551.2 [M + H]$^+$. |

TABLE 3-continued

| Example | Structural formula | Analysis data |
| --- | --- | --- |
| 46 | | ¹H-NMR (300 MHz, DMSO-d₆) δ 8.98 (s, 1H), 8.36-8.30 (m, 2H), 7.92 (m, 1H), 7.62 (m, 1H), 7.49-7.25 (m, 3H), 7.02-6.92 (m, 2H), 6.34 (m, 1H), 3.34 (q, 2H), 3.26 (s, 3H), 2.98 (m, 4H), 2.56 (m, 4H), 2.28 (s, 3H), 1.28 (t, 3H); MS (ESI⁺): m/z = 539.2 [M + H]⁺. |
| 47 | | ¹H-NMR (300 MHz, DMSO-d₆) δ 8.90 (s, 1H), 8.32 (s, 1H), 8.16 (d, 1H), 7.85 (m, 1H), 7.54 (m, 1H), 7.41 (m, 1H), 7.32-7.21 (m, 2H), 6.95-6.84 (m, 2H), 6.28 (m, 1H), 3.56 (m, 1H), 3.20 (s, 3H), 2.92 (m, 4H), 2.50 (m, 4H), 2.22 (s, 3H), 1.23 (d, 6H); MS (ESI⁺): m/z = 553.2 [M + H]⁺. |
| 48 | | ¹H-NMR (300 MHz, DMSO-d₆) δ 11.32 (s, 1H), 8.92 (s, 1H), 8.34 (d, 1H), 8.19 (s, 1H), 7.85 (m, 1H), 7.61 (d, 1H), 7.40-7.15 (m, 3H), 6.94-6.85 (m, 2H), 6.25 (d, 1H), 3.21 (s, 3H), 2.91 (m, 4H), 2.82 (m, 1H), 2.48 (m, 4H), 2.21 (s, 3H), 1.00 (m, 2H), 0.87 (m, 2H); MS (ESI⁺): m/z = 551.2 [M + H]⁺. |
| 49 | | ¹H-NMR (300 MHz, DMSO-d₆) δ 11.31 (s, 1H), 9.22 (br, 1H), 8.87 (s, 1H), 8.74 (s, 1H), 7.94 (d, 1H), 7.83 (d, 1H), 7.18-7.41 (m, 4H), 6.95 (m, 1H), 6.88 (t, 1H), 6.36 (s, 1H), 2.91 (m, 4H), 2.87 (s, 3H), 2.50 (m, 4H), 2.36 (q, 2H), 1.03 (t, 3H); MS (ESI⁺): m/z = 525.2 [M + H]⁺. |

TABLE 3-continued

| Example | Structural formula | Analysis data |
|---|---|---|
| 50 | 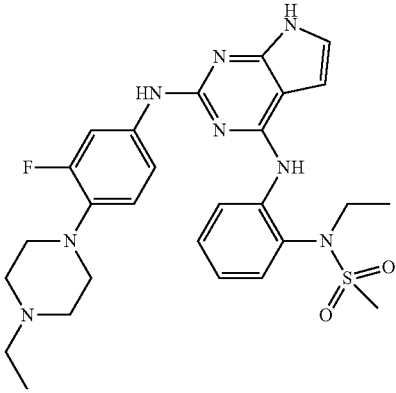 [SMILES: CCN1CCN(c2ccc(Nc3nc(Nc4ccccc4N(CC)S(C)(=O)=O)c4cc[nH]c4n3)cc2F)CC1] | ¹H-NMR (300 MHz, DMSO-d₆) δ 11.30 (s, 1H), 8.89 (s, 1H), 8.28 (s, 1H), 8.23 (d, 1H), 7.87 (d, 1H), 7.57 (d, 1H), 7.42 (t, 1H), 7.37 (m, 1H), 7.24 (t, 1H), 6.96 (m, 1H), 6.89 (m, 1H), 6.27 (d, 1H), 3.55 (m, 2H), 3.30 (m, 4H), 3.11 (s, 3H), 3.00 (m, 2H), 2.88 (m, 4H), 1.21 (t, 6H); MS (ESI⁺): m/z = 553.2 [M + H]⁺. |
| 51 | 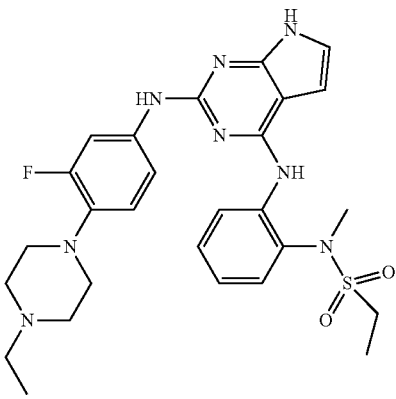 [SMILES: CCN1CCN(c2ccc(Nc3nc(Nc4ccccc4N(C)S(=O)(=O)CC)c4cc[nH]c4n3)cc2F)CC1] | ¹H-NMR (300 MHz, DMSO-d₆) δ 8.88 (s, 1H), 8.22 (m, 2H), 7.83 (m, 1H), 7.54 (m, 1H), 7.38 (m, 1H), 7.30 (m, 1H), 7.19 (m, 1H), 6.95-6.84 (m, 2H), 6.26 (m, 1H), 3.27 (q, 2H), 3.18 (s, 3H), 2.91 (m, 4H), 2.50 (m, 4H), 2.34 (q, 2H), 1.21 (t, 3H), 1.01 (t, 3H); MS (ESI⁺): m/z = 553.2 [M + H]⁺. |
| 52 | 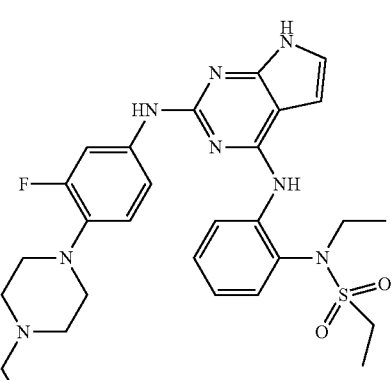 | ¹H-NMR (300 MHz, DMSO-d₆) δ 11.38 (s, 1H), 8.98 (s, 1H), 8.44 (d, 1H), 8.05 (s, 1H), 7.88 (d, 1H), 7.55 (d, 1H), 7.33 (t, 1H), 7.24 (d, 1H), 7.19 (t, 1H), 6.99 (m, 1H), 6.95 (m, 1H), 6.18 (d, 1H), 3.68 (m, 2H), 2.95 (m, 4H), 2.52 (m, 6H), 2.39 (m, 2H), 1.29 (t, 3H), 1.04 (t, 3H), 1.01 (t, 3H); MS (ESI⁺): m/z = 567.2 [M + H]⁺. |
| 53 | 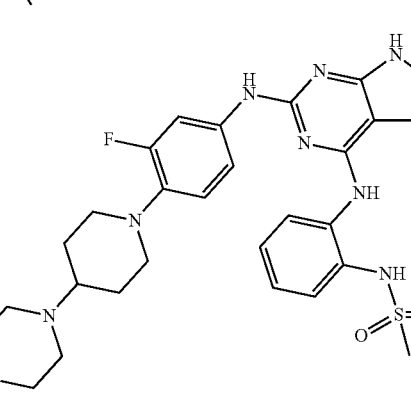 | ¹H-NMR (300 MHz, DMSO-d₆) δ 11.31 (s, 1H), 8.86 (s, 1H), 8.75 (s, 1H), 7.91 (m, 1H), 7.80 (m, 1H), 7.40 (m, 1H), 7.29 (m, 2H), 7.19 (m, 1H), 6.96-6.85 (m, 2H), 6.36 (m, 1H), 3.32 (m, 4H), 2.88 (s, 3H), 2.52 (m, 4H), 2.45-2.27 (m, 7H), 1.82 (m, 2H), 1.55 (m, 2H), 1.11 (t, 3H); MS (ESI⁺): m/z = 608.3 [M + H]⁺. |

TABLE 3-continued

| Example | Structural formula | Analysis data |
|---|---|---|
| 54 | | $^1$H-NMR (300 MHz, DMSO-d$_6$) δ 8.91 (s, 1H), 8.27 (m, 2H), 7.84 (dd, 1H), 7.56 (m, 1H), 7.40 (m, 1H), 7.29 (m, 1H), 7.22 (m, 1H), 6.97-6.89 (m, 2H), 6.28 (m, 1H), 3.32-3.16 (m, 6H), 3.20 (s, 3H), 2.63-2.50 (m, 4H), 2.41 (m, 7H), 1.82 (m, 2H), 1.57 (m, 2H), 1.22 (t, 3H), 1.00 (t, 3H); MS (ESI$^+$): m/z = 636.3 [M + H]$^+$. |
| 55 | | $^1$H-NMR (300 MHz, DMSO-d$_6$) δ 11.38 (s, 1H), 8.97 (s, 1H), 8.49 (d, 1H), 7.99 (s, 1H), 7.87 (d, 1H), 7.55 (d, 1H), 7.40 (d, 1H), 7.32 (d, 1H), 7.20 (t, 1H), 7.00 (m, 1H), 6.98 (m, 1H), 6.17 (d, 1H), 3.14 (s, 3H), 2.89 (m, 4H), 2.48 (m, 4H), 1.50 (m, 10H), 1.23 (m, 2H), 1.03 (t, 3H), 0.99 (t, 3H); MS (ESI$^+$): m/z = 621.3 [M + H]$^+$. |
| 56 | | $^1$H-NMR (300 MHz, DMSO-d$_6$) δ 11.38 (s, 1H), 8.98 (s, 1H), 8.50 (d, 1H), 7.99 (s, 1H), 7.88 (d, 1H), 7.56 (d, 1H), 7.41 (t, 1H), 7.34 (d, 1H), 7.21 (t, 1H), 6.98 (m, 1H), 6.87 (d, 1H), 6.17 (d, 1H), 3.64 (m, 2H), 3.30 (m, 4H), 3.13 (s, 3H), 2.94 (m, 4H), 2.50 (m, 2H), 2.40 (m, 2H), 1.24 (m, 2H), 1.03 (t, 3H), 0.94 (t, 3H), 0.85 (m, 2H); MS (ESI$^+$): m/z = 607.3 [M + H]$^+$. |

The compounds of Examples 57 to 64 as represented in Table 4 were prepared in the same or similar manner as the method of Example 1, except that 2,4-dichloro-7H-pyrrolo[2,3-d]pyrimidine substituted with R$_3$ (wherein R$_3$ is as defined herein) was used instead of 2,4-dichloro-7H-pyrrolo[2,3-d]pyrimidine used in step 3) of Example 1, and various derivatives represented by halogen-substituted Cy$_2$-NO$_2$ and Y—H (Cy$_2$ and Y are as defined herein) were used instead of 4-fluoronitrobenzene and 1-methyl-4-piperazine used in step 5).

TABLE 4

| Example | Structural formula | Analysis data |
|---|---|---|
| 57 | | $^1$H-NMR (300 MHz, DMSO-d$_6$) δ 8.80 (s, 1H), 8.73 (d, 1H), 8.35 (brs, 1H), 7.65 (m, 1H), 7.41-7.31 (m, 2H), 7.16-7.07 (m, 2H), 6.92 (t, 1H), 6.75 (m, 2H), 3.30 (s, 3H), 3.12 (m, 4H), 3.01 (s, 3H), 2.67 (m, 4H), 2.40 (s, 3H); MS (ESI$^+$): m/z = 559.2 [M + H]$^+$. |
| 58 | | $^1$H-NMR (300 MHz, DMSO-d$_6$) δ 11.57 (s, 1H), 8.75 (d, 1H), 8.70 (d, 2H), 7.57 (d, 1H), 7.27 (m, 2H), 7.10 (d, 2H), 6.81 (t, 1H), 3.21 (s, 3H), 3.13 (s, 3H), 3.05 (m, 4H), 2.48 (m, 4H), 2.25 (s, 3H); MS (ESI+): m/z = 577.2 [M + H]$^+$. |
| 59 | | $^1$H-NMR (300 MHz, DMSO-d$_6$) δ 11.51 (s, 1H), 8.90-8.85 (m, 2H), 8.75 (s, 1H), 8.43 (d, 1H), 7.89 (m, 1H), 7.58 (m, 1H), 7.33 (m, 1H), 7.13-7.07 (m, 2H), 6.80 (d, 1H), 3.38 (m, 4H), 3.20 (s, 3H), 3.12 (s, 3H), 2.39 (m, 4H), 2.21 (s, 3H; MS (ESI$^+$): m/z = 542.2 [M + H]$^+$. |
| 60 | | $^1$H-NMR (300 MHz, DMSO-d$_6$) δ 11.05 (s, 1H), 8.99 (s, 1H), 8.91 (d, 1H), 8.19 (s, 1H), 7.89 (m, 1H), 7.61 (d, 1H), 7.42-7.31 (m, 2H), 7.13 (m, 1H), 6.94 (m, 1H), 6.72 (d, 1H), 3.24 (s, 3H), 3.15 (s, 3H), 2.95 (m, 4H), 2.47 (m, 4H), 2.47 (s, 3H), 2.24 (s, 3H); MS (ESI$^+$): m/z = 539.2 [M + H]$^+$. |

TABLE 4-continued

| Example | Structural formula | Analysis data |
|---|---|---|
| 61 | | $^1$H-NMR (300 MHz, DMSO-$d_6$) δ 12.25 (s, 1H), 9.29 (s, 1H), 8.65 (d, 1H), 8.16 (s, 1H), 8.00 (s, 1H), 7.82 (d, 1H), 7.61 (d, 1H), 7.41 (t, 1H), 7.31 (d, 1H), 7.19 (t, 1H), 6.94 (t, 1H), 3.21 (s, 3H), 3.12 (s, 3H), 2.94 (m, 4H), 2.50 (m, 4H), 2.22 (s, 3H); MS (ESI$^+$): m/z = 550.2 [M + H]$^+$. |
| 62 | | $^1$H-NMR (300 MHz, DMSO-$d_6$) δ 11.15 (s, 1H), 9.13 (s, 1H), 8.76 (d, 1H), 8.17 (s, 1H), 7.84 (d, 1H), 7.60 (d, 1H), 7.38 (d, 1H), 7.32 (d, 1H), 7.17 (t, 1H), 6.95 (d, 1H), 6.88 (d, 1H), 3.21 (s, 3H), 3.12 (s, 3H), 2.95 (m, 4H), 2.48 (m, 4H), 2.23 (s, 3H); MS (ESI+): m/z = 543.2 [M + H]$^+$. |
| 63 | | $^1$H-NMR (300 MHz, DMSO-$d_6$) δ 11.10 (s, 1H), 9.12 (s, 1H), 8.75 (m, 1H), 8.17 (m, 1H), 7.84 (dd, 1H), 7.61 (dd, 1H), 7.40 (m, 1H), 7.38 (m, 1H), 7.18 (m, 1H), 6.98-6.88 (m, 2H), 3.22 (s, 3H), 3.13 (s, 3H), 2.97 (m, 4H), 2.51 (m, 4H), 2.39 (m, 2H), 1.04 (t, 3H); MS (ESI+): m/z = 557.2 [M + H]$^+$. |
| 64 | | $^1$H-NMR (300 MHz, DMSO-$d_6$) δ 9.10 (s, 1H), 8.76 (d, 1H), 8.17 (d, 1H), 7.85 (m, 1H), 7.61 (m, 1H), 7.42 (m, 1H), 7.32 (m, 1H), 7.18 (m, 1H), 6.98-6.87 (m, 2H), 3.32 (m, 4H), 3.22 (s, 3H), 3.13 (s, 3H), 2.57 (m, 4H), 2.37 (m, 5H), 2.18 (m, 3H), 1.85 (m, 2H), 1.57 (m, 2H); MS (ESI+): m/z = 626.3 [M + H]$^+$. |

Example 65: Preparation of N-(2-((2-((3-fluoro-4-(4-(4-methylpiperazin-1-yl)piperidin-1-yl)phenyl)amino)-7-methyl-7H-pyrrolo[2,3-d]pyrimidine-4-yl)amino)phenyl)-N-methylmethanesulfonamide

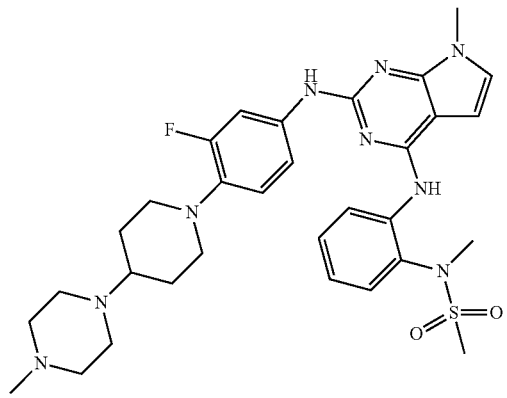 [SMILES: CN1CCN(C2CCN(c3ccc(Nc4nc(Nc5ccccc5N(C)S(C)(=O)=O)c5ccn(C)c5n4)cc3F)CC2)CC1]

Step 1) Preparation of 2,4-dichloro-7-methyl-7H-pyrrolo[2,3-d]pyrimidine 500 mg (2.66 mmol) of 2,4-dichloro-7H-pyrrolo[2,3-d]pyrimidine was diluted with 2.5 ml of acetonitrile, and 1.52 g (2.79 mmol) of sodium hydride was slowly added at 0° C. and then stirred for 30 minutes. 180 ml (2.93 mmol) of iodomethane was added to the reaction mixture and then stirred at room temperature for 1 hour. After the reaction was completed, the resulting mixture was slowly added dropwise into ice water and then stirred. The resulting solid was washed with distilled water, filtered under reduced pressure, and dried under reduced pressure to obtain 500 mg of the compound of the title (Yield: 93%).

$^1$H-NMR (300 MHz, CDCl$_3$) δ 7.21 (s, 1H), 6.63 (s, 1H), 3.88 (s, 3H).

Step 2

Preparation of N-(2-((2-((3-fluoro-4-(4-(4-methylpiperazin-1-yl)piperidin-1-yl)phenyl)amino)-7-methyl-7H-pyrrolo[2,3-d]pyrimidine-4-yl)amino)phenyl)-N-methylmethanesulfonamide 40 mg of the compound of the title (Yield: 47%) was obtained through the same process as in step 4) to step 7) of Example 1, except that the compound of step 1) was used instead of 2,4-dichloro-7-((2-(trimethylsilyl)ethoxy)methyl)-7H-pyrrolo[2,3-d]pyrimidine used in step 4) of Example 1, and 3,3-fluoro-4-(4-(4-methylpiperazin-1-yl)piperidin-1-yl)aniline was used instead of 4-(4-methylpiperazin-1-yl)aniline used in step 7) of Example 1.

$^1$H-NMR (300 MHz, CDCl$_3$) δ 8.51 (d, 1H), 8.08 (s, 1H), 7.82 (d, 1H), 7.43 (t, 1H), 7.30 (m, 1H), 7.09-7.18 (m, 2H), 6.90 (t, 1H), 6.77-6.83 (m, 2H), 6.39 (s, 1H), 3.76 (s, 3H), 3.46 (m, 2H), 3.30 (s, 3H), 3.02 (s, 3H), 2.65-2.76 (m, 11H), 2.38 (s, 3H), 1.75-1.99 (m, 4H);

MS (ESI+): m/z=622.3 [M+H]$^+$.

Example 66

Preparation of N-(2-((2-((3-fluoro-4-(4-methylpiperazin-1-yl)phenyl)amino)-9H-purine-6-yl)amino)phenyl)-N-methylmethanesulfonamide

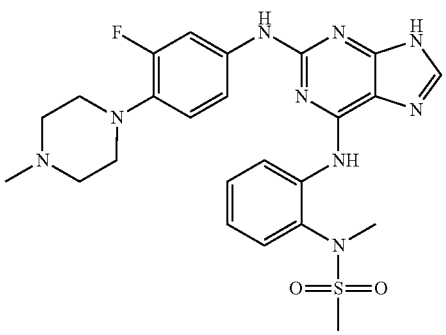 [SMILES: CN1CCN(c2ccc(Nc3nc(Nc4ccccc4N(C)S(C)(=O)=O)c4nc[nH]c4n3)cc2F)CC1]

Step 1) Preparation of N-(2-((2-chloro-9-(tetrahydro-2H-pyran-2-yl)-9H-purine-6-yl)amino)phenyl)-N-methylmethanesulfonamide 130 mg of the compound of the title (Yield: 27%) was obtained through the same process as in step 4) of Example 1, except that 2,6-dichloro-9-(tetrahydro-2H-pyran-2-yl)-9H-purine (preparation method of US 20160083369) was used instead of 2,4-dichloro-7-((2-(trimethylsilyl)ethoxy)methyl)-7H-pyrrolo[2,3-d]pyrimidine used in step 4) of Example 1.

$^1$H-NMR (300 MHz, DMSO-d6) δ 9.19 (s, 1H), 8.53 (s, 1H), 8.13 (d, 1H), 7.66 (d, 1H), 7.49 (t, 1H), 7.32 (t, 1H), 5.66 (d, 1H), 4.04 (m, 1H), 3.76 (m, 1H), 3.21 (s, 3H), 3.06 (s, 3H), 2.31-2.22 (m, 1H), 2.04 (m, 2H), 1.77 (m, 1H), 1.59 (m, 2H).

Step 2) Preparation of 3-fluoro-4-(4-methylpiperazin-1-yl)aniline 4.5 g of the compound of the title (Yield: 85%) was obtained through the same process as in step 4) to step 6) of Example 1, except that 3,4-difluoronitrobenzene was used instead of 4-fluoronitrobenzene used in step 5) of Example 1.

$^1$H-NMR (300 MHz, DMSO-d6) δ 6.77 (t, 1H), 6.34 (m, 2H), 4.93 (s, 2H), 2.81 (m, 4H), 2.40 (m, 4H), 2.18 (s, 3H).

Step 3) Preparation of N-(2-((2-((3-fluoro-4-(4-methylpiperazin-1-yl)phenyl)amino)-9-(tetrahydro-2H-pyran-2-yl)-9H-purine-6-yl)amino)phenyl)-N-methylmethanesulfonamide 100 mg (0.229 mmol) of the compound prepared in step 1) and 45 mg (0.217 mmol) of the compound prepared in step 2) were diluted with 6 ml of 1,4-dioxane, and 21 mg (0.023 mmol) of tris(dibenzylideneacetone)dipalladium(0) and 29 mg (0.046 mmol) of (±)-2,2'-bis(diphenylphosphino)-1,1'-binaphthyl were added thereto and stirred at room temperature for 10 minutes, and thereafter 44 mg (0.458 mmol) of tert-butoxy sodium was added thereto, sealed, and stirred at 100° C. for 18 hours. After the reaction was completed, the resulting reaction mixture was cooled down to room temperature, washed with a mixed solvent of chloroform and 2-propanol (3:1 (volume ratio)) in a Celite-filled filter, and filtered under reduced pressure, and then the resulting filtrate was washed with saturated brine. The resulting separated organic layer was dried with anhydrous sodium sulfate, and then filtered under reduced pressure and distilled under reduced pressure. The obtained residue was separated by column chromatography (chloroform:methanol=40:1 (volume ratio)) to obtain 120 mg of the compound of the title (Yield: 86%).

$^1$H-NMR (300 MHz, DMSO-d6) δ 9.32 (s, 1H), 8.63 (d, 1H), 8.56 (s, 1H), 8.18 (s, 1H), 7.88 (d, 1H), 7.64 (m, 1H), 7.44-7.33 (m, 2H), 7.21 (t, 1H), 6.99 (t, 1H), 5.58 (m, 1H), 4.08 (m, 1H), 3.71 (m, 1H), 3.22 (s, 3H), 3.13 (s, 3H), 2.99 (m, 4H), 2.58 (m, 4H), 2.32 (m, 1H), 2.30 (s, 3H), 2.00 (m, 2H), 1.70-1.62 (m, 3H).

Step 4) Preparation of N-(2-((2-((3-fluoro-4-(4-methylpiperazin-1-yl)phenyl)amino)-9H-purine-6-yl)amino)phenyl)-N-methylmethanesulfonamide 60 mg (0.098 mmol) of the compound prepared in step 3) was distilled in 5 ml of dichloromethane and cooled down to 0° C., and thereafter, 1.0 ml of trifluoroacetic acid was added and stirred at room temperature for 1 hour. After the reaction was completed, the resulting reaction mixture was distilled under reduced pressure, and then distilled with a mixed solvent of chloroform and 2-propanol (3:1 (volume ratio)) and washed sequentially with a saturated sodium bicarbonate aqueous solution and distilled water. The resulting separated organic layer was dried with anhydrous sodium sulfate, and then filtered under reduced pressure and distilled under reduced pressure. The obtained residue was separated by column chromatography (chloroform:methanol=5:1 (volume ratio)) to obtain 15 mg of the compound of the title (Yield: 29%).

$^1$H-NMR (300 MHz, DMSO-d6) δ 12.7 (s, 1H), 9.19 (s, 1H), 8.73 (d, 1H), 8.51 (s, 1H), 7.96 (s, 1H), 7.89 (d, 1H), 7.63 (d, 1H), 7.43 (t, 1H), 7.35 (dd, 1H), 7.20 (t, 1H), 7.00 (t, 1H), 3.23 (s, 3H), 3.14 (s, 3H), 3.00 (m, 4H), 2.73 (m, 4H), 2.35 (s, 3H);

MS (ESI+): m/z=526.2 [M+H]$^+$.

Example 67

Preparation of N-(2-((6-((3-fluoro-4-(4-methylpiperazin-1-yl)phenyl)amino)-1H-pyrazolo[3,4-d]pyrimidine-4-yl)amino)phenyl)-N-methylmethanesulfonamide

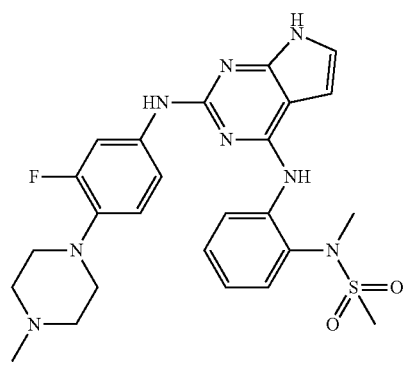 [SMILES: CN1CCN(c2ccc(Nc3nc(Nc4ccccc4N(C)S(C)(=O)=O)c4cc[nH]c4n3)cc2F)CC1]

12 mg of the compound of the title (Final step yield: 21%) was obtained through the same process as in Example 66, except that 4,6-dichloro-1-(tetrahydro-2H-pyran-2-yl)-1H-pyrazolo[3,4-d]pyrimidine (preparation method of WO2014140065) was used instead of 2,6-dichloro-9-(tetrahydro-2H-pyran-2-yl)-9H-purine used in step 1) of Example $^1$H-NMR (300 MHz, DMSO-d6) δ 13.0 (s, 1H), 9.11 (s, 1H), 9.04 (s, 1H), 7.87 (m, 1H), 7.79 (m, 2H), 7.58 (m, 1H), 7.43 (m, 1H), 7.29 (m, 2H), 6.88 (t, 1H), 3.28 (m, 4H), 3.15 (s, 3H), 3.01 (s, 3H), 2.93 (m, 4H), 2.23 (s, 3H);

MS (ESI+): m/z=526.2 [M+H]$^+$.

Experimental Example 1: Ba/F3 EGFR del19/T790M/C797S Cell Growth Inhibition Test In order to identify whether the compounds obtained in Examples 1 to 67 exhibit activity against cells expressing EGFR del19/T790M/C797S mutation, a growth inhibitory effect was confirmed in Ba/F3 cell lines overexpressing the EGFR del19/T790M/C797S mutations (CrownBio) as follows. For cell growth conditions, an RPMI Medium 1640 (1×) containing 10% FBS and 1% penicillin/straptomycin (Gibco BRL) was used.

Specifically, the cell line stored in a liquid nitrogen tank was taken out, rapidly dissolved at 37° C., and thereafter centrifuged to remove the cryopreservation medium. The recovered cell pellets were well mixed in a culture medium, put into a culture flask, and passaged under conditions of 37° C. and 5% carbon dioxide to stabilize the cells to the logarithmic growth phase. Thereafter, cells were taken from the flask, centrifuged to remove the culture medium, washed with Dulbecco's phosphate buffered saline (DPBS), and then centrifuged again to remove DPBS, and then diluted with a culture medium to have 1×10$^5$ cells/ml. The diluted cells were dispensed into a 96-well plate at 100 μl per well. The compounds prepared in the above examples were each dissolved in 99.5% dimethylsulfoxide (hereinafter, DMSO, cell culture grade) to a concentration of 10 mM. The DMSO solution containing each compound was diluted with a culture medium to a concentration of 30 μM, and then tenfold serial dilution was used to prepare a solution diluted upto 0.3 nM (in order to reach a final DMSO concentration of 1% or less).

50 μl of a test solution of each compound was added each time to the 96-well plate in which the cells were dispensed, thus reaching a final concentration of 10 μM to 0.1 nM in 150 μl per well. The cells treated with the test solution were cultured under conditions of 37° C. and 5% carbon dioxide for 72 hours. After the 96-well plate in which the cells were cultured was acclimated to room temperature for 30 minutes, CellTiter-Glo® Luminescent Cell Assay Reagent (CTG, Promega) was dispensed at 50 μl per well. After stabilizing luminescence signals for 10 minutes, the luminescence intensity was measured with a microplate reader.

Based on the measured value, a GI$_{50}$ value of each compound, which is the concentration at which cell growth is inhibited by 50%, was calculated with respect to 100% of the value obtained by subtracting the initial cell density value from the final cell density value of a well not treated with a test material. The GI50 value of each compound was calculated using nonlinear regression of GraphPad Prism; log[inhibitor] vs. normalized response analysis. The results are shown in Table 5.

TABLE 5

| Example | Ba/F3 EGFR del19/T790M/C797S cells, GI$_{50}$, nM |
|---|---|
| 1 | 3.1 |
| 2 | 522 |
| 3 | 157 |
| 4 | 453 |
| 5 | 31 |
| 6 | 54 |
| 7 | 19 |
| 8 | 10 |
| 12 | 4.2 |
| 13 | 11 |
| 14 | 15 |
| 18 | 73 |
| 19 | 112 |
| 20 | 37 |
| 21 | 17 |
| 22 | 371 |
| 23 | 76 |
| 24 | 47 |
| 25 | 22 |
| 27 | 6 |
| 28 | 7 |
| 29 | 626 |
| 30 | 9.4 |
| 31 | 10 |
| 32 | 11 |
| 33 | 31 |
| 34 | 6 |
| 35 | 185 |
| Erlotinib | >5,000 |
| 36 | 20 |
| 37 | 95 |
| 38 | 25 |
| 39 | 67 |
| 40 | 65 |
| 41 | 141 |
| 42 | 123 |
| 43 | 37 |
| 44 | 72 |
| 45 | 64 |
| 46 | 16 |
| 47 | 49 |
| 48 | 30 |
| 50 | 26 |
| 51 | 25 |
| 52 | 119 |
| 53 | 7 |
| 57 | 7.9 |
| 58 | 93 |
| 59 | 41 |
| 60 | 15 |
| 61 | 46 |
| 62 | 46 |
| 63 | 64 |
| 64 | 28 |
| 66 | 63 |
| 67 | 254 |
| Osimertinib | 1,124 |
| Afatinib | 776 |

Experimental Example 2: PC9 EGFR del19/T790M/C797S Cell Growth Inhibition Test In order to identify whether the compounds obtained in Examples 1 to 67 exhibit activity against cells expressing EGFR del19/T790M/C797S mutation, a growth inhibitory effect was found in PC9 cell lines overexpressing the EGFR del19/T790M/C797S mutation (CrownBio) as follows. For cell growth conditions, an RPMI Medium 1640 (1×) containing 10% FBS and 1% penicillin/straptomycin (Gibco BRL) was used.

Specifically, the cell line stored in a liquid nitrogen tank was taken out, rapidly dissolved at 37° C., and thereafter centrifuged to remove the cryopreservation medium. The recovered cell pellets were well mixed in a culture medium, put into a culture flask, and passaged under conditions of 37° C. and 5% carbon dioxide to stabilize the cells to logarithmic cell growth phase. Thereafter, cells were taken from the flask, centrifuged to remove the culture medium, washed with Dulbecco's phosphate buffered saline (DPBS), and then centrifuged again to remove DPBS, and then diluted with a culture medium to have 1×10$^5$ cells/ml. The diluted cells were dispensed into a 96-well plate at 100 μl per well. The compounds prepared in the above examples were each dissolved in 99.5% dimethylsulfoxide (hereinafter, DMSO, cell culture grade) to a concentration of 10 mM. The DMSO solution containing each compound was diluted with a culture medium to a concentration of 30 μM, and then tenfold serial dilution was used to prepare a solution diluted upto 0.3 nM (in order to reach a final DMSO concentration of 1% or less).

50 μl of a test solution of each compound was added each time to the 96-well plate in which the cells were dispensed, so that a final concentration of 10 μM to 0.1 nM was reached in 150 μl per well. The cells treated with the test solution were cultured under conditions of 37° C. and 5% carbon dioxide for 72 hours. After the 96-well plate in which the cells were cultured was acclimated to room temperature for 30 minutes, CellTiter-Glo® Luminescent Cell Assay Reagent (CTG, Promega) was dispensed at 50 μl per well. After stabilizing luminescence signals for 10 minutes, the luminescence intensity was measured with a microplate reader.

Based on the measured value, a 6150 value of each compound, which is the concentration at which cell growth is inhibited by 50%, was calculated with respect to 100% of the value obtained by subtracting the initial cell density value of a well not treated with a test material from the final cell density value thereof. The GI50 value of each compound was calculated using nonlinear regression of Graph-Pad Prism; log[inhibitor] vs. normalized response analysis. The results are shown in Table 6.

TABLE 6

| Example | PC9 EGFR del19/T790M/C797S cells, GI$_{50}$, nM |
|---|---|
| 8 | 201 |
| 9 | 420 |
| 10 | 538 |
| 11 | 641 |
| 13 | 267 |
| 14 | 126 |
| 15 | 131 |
| 16 | 160 |
| 17 | 311 |
| 26 | 369 |
| 42 | 951 |
| 49 | 858 |
| 53 | 698 |
| 54 | 530 |
| 56 | 564 |
| 65 | 3,376 |

Experimental Example 3: EGFR Enzyme Inhibitory Activity Evaluation

An enzyme activity inhibition evaluation was performed to identify whether the compounds obtained in the above examples exhibit EGFR normal (WT) or mutant (T790M/

L858R, L858R/T790M/C797S) inhibitory activity. For this, a Z'-LYTE kinase assay kit (ThermoFisher Scientific, PV3191) was used, and the kinases used were purchased from Thermo Fisher Scientific Inc. A simple test method is summarized as follows.

The compounds prepared in Examples 1 to 47 were each dissolved in DMSO to make a 10 mM solution, and diluted with an aqueous solution of 4% DMSO to 1/10 to a concentration of 10 μM to 0.0001 μM. Each kinase was diluted to a concentration of 7-45 ng/assay using a kinase buffer (50 mM HEPES (pH 7.5), 10 mM $MgCl_2$, 4 mM $MnCl_2$, 2 mM DTT, 1 mM EGTA, 0.01% BRIJ-35, or 50 mM HEPES (pH 6.5), 10 mM $MgCl_2$, 1 mM EGTA, 0.01% BRIJ-35, 0.02% $NaN_3$). The test was performed on 384 well plates (well polystyrene flat-bottomed plates). First, after 5 μl of a diluted compound solution was added, a protein substrate at a concentration as specified in the kit, 10 μl of a kinase mixed solution, and 5 μl of a 10-100 μM ATP solution were added to the sample and reacted at room temperature for 60 minutes in a stirrer. Thereafter, 10 μl of a coloring solution was added each to cause a fluorescence reaction of the peptide substrate for 60 minutes, and 10 μl of a stopping solution was added each to terminate the reaction. Fluorescence values of the plates were measured using a microplate reader such as SynergyNeo (Biotek) (400 nm excitation filter, 445/520 nm emission filter). At this time, according to the protocol in the kit, the degree of kinase reaction inhibitory activity of the compounds was calculated as a phosphorylation rate by percentage (0-100%) with respect to a control group, and concentration sections on x-axis in which the activity is inhibited by 50% were obtained to calculate 50% inhibitory concentration ($IC_{50}$) values. For the calculation of the $IC_{50}$ value of each compound and analysis of the results, Microsoft Excel and GraphPad Prism were used. The results are shown in Table 7.

TABLE 7

| | EGFR Kinase, $IC_{50}$, nM | | |
|---|---|---|---|
| Example | L858R/T790M/C797S | T790M/L858R | WT |
| 14 | 4 | 2.9 | 4,492 |
| 16 | 4 | 2.7 | 1,526 |
| 36 | 13 | 12 | 2,185 |
| Afatinib | 120 | 7.6 | 3.3 |

In order to identify whether a compound according to the present invention exhibits activity against cells expressing an EGFR mutation, a growth inhibitory effect was identified in the Ba/F3 cell line and PC9 cell line overexpressing EGFR del19/T790M/C797S mutations (Experimental Examples 1 and 2). As shown in Tables 4 and 5, in the BaF3 cell line and PC9 cell line having EGFR del19/T790M/C797S mutations, a very excellent proliferation inhibitory effect was observed. As EGFR inhibitors, erlotinib, a first-generation drug, and osimertinib, a third-generation drug, did not show proliferation inhibitory activity in the BaF3 cell line with EGFR del19/T790M/C797S mutation as shown in Table 4 (GI50>1,000 nM). However, a majority of the compounds according to the present invention showed excellent cell proliferation inhibitory effects with a GI50 value of less than 100 nM in the BaF3 cell line and PC9 cell line with EGFR del19/T790M/C797S mutations. Afatinib as a second-generation drug showed inhibitory activity, but such a quinazoline based irreversible inhibitor has serious side effects (diarrhea, skin disease, and weight loss) caused by pharmacological actions resulting from strong simultaneous inhibitory activity against both EGFR WT and EGFR mutations at a dosage for EGFR mutation inhibition. In order to evaluate the possibility to avoid the side effects caused by such EGFR WT inhibition, selectivity for EGFR WT and EGFR mutations were evaluated (Experimental Example 3). As shown in Table 6, the compounds according to the present invention exhibited excellent inhibitory effects against EGFR L858R/T790M/C797S and L858R/T790M mutations, but no inhibitory effect against EGFR WT, and thus has very high selectivity for mutations. It was found that the compounds according to the present invention have incomparably superior selectivity as compared to afatinib. Therefore, it can be confirmed that the compound according to the present invention is a safer and more effective drug for patients with non-small cell lung cancer with EGFR mutation.

The invention claimed is:
1. A compound selected from the group consisting of compounds 1) to 67):
 1) N-methyl-N-(2-((2-((4-(4-methylpiperazin-1-yl)phenyl)amino)-7H-pyrrolo[2,3-d]pyrimidine-4-yl)amino)phenyl)methanesulfonamide;
 2) N-methyl-N-(2-((2-((2-methyl-4-(4-methylpiperazin-1-yl)phenyl)amino)-7H-pyrrolo[2,3-d]pyrimidine-4-yl)amino)phenyl)methanesulfonamide;
 3) N-(2-((2-((2-fluoro-4-(4-methylpiperazin-1-yl)phenyl)amino)-7H-pyrrolo[2,3-d]pyrimidine-4-yl)amino)phenyl)-N-methylmethanesulfonamide;
 4) N-(2-((2-((3-hydroxy-4-(4-methylpiperazin-1-yl)phenyl)amino)-7H-pyrrolo[2,3-d]pyrimidine-4-yl)amino)phenyl)-N-methylmethanesulfonamide;
 5) N-methyl-N-(2-((2-((3-methyl-4-(4-methylpiperazin-1-yl)phenyl)amino)-7H-pyrrolo[2,3-d]pyrimidine-4-yl)amino)phenyl)methanesulfonamide;
 6) N-(2-((2-((3-chloro-4-(4-methylpiperazin-1-yl)phenyl)amino)-7H-pyrrolo[2,3-d]pyrimidine-4-yl)amino)phenyl)-N-methylmethanesulfonamide;
 7) N-(2-((2-((3-fluoro-4-(4-methylpiperazin-1-yl)phenyl)amino)-7H-pyrrolo[2,3-d]pyrimidine-4-yl)amino)phenyl)-N-methylmethanesulfonamide;
 8) N-(2-((2-((3-fluoro-4-(4-ethylpiperazin-1-yl)phenyl)amino)-7H-pyrrolo[2,3-d]pyrimidine-4-yl)amino)phenyl)-N-methylmethanesulfonamide;
 9) N-(2-((2-((3-fluoro-4-(4-isopropylpiperazin-1-yl)phenyl)amino)-7H-pyrrolo[2,3-d]pyrimidine-4-yl)amino)phenyl)-N-methylmethanesulfonamide;
 10) N-(2-((2-((3-fluoro-4-(4-propylpiperazin-1-yl)phenyl)amino)-7H-pyrrolo[2,3-d]pyrimidine-4-yl)amino)phenyl)-N-methylmethanesulfonamide;
 11) N-(2-((2-((3-fluoro-4-(4-cyclopropylpiperazin-1-yl)phenyl)amino)-7H-pyrrolo[2,3-d]pyrimidine-4-yl)amino)phenyl)-N-methylmethanesulfonamide;
 12) N-(2-((2-((3-fluoro-4-morpholinophenyl)amino)-7H-pyrrolo[2,3-d]pyrimidine-4-yl)amino)phenyl)-N-methylmethanesulfonamide;
 13) N-(2-((2-((3-fluoro-4-(4-(4-methylpiperazin-1-yl)piperidin-1-yl)phenyl)amino)-7H-pyrrolo[2,3-d]pyrimidine-4-yl)amino)phenyl)-N-methylmethanesulfonamide;
 14) N-(2-((2-((3-fluoro-4-(4-(4-ethylpiperazin-1-yl)piperidin-1-yl)phenyl)amino)-7H-pyrrolo[2,3-d]pyrimidine-4-yl)amino)phenyl)-N-methylmethanesulfonamide;

15) N-(2-((2-((3-fluoro-4-(4-(4-isopropylpiperazin-1-yl)piperidin-1-yl)phenyl)amino)-7H-pyrrolo[2,3-d]pyrimidine-4-yl)amino)phenyl)-N-methylmethanesulfonamide;

16) N-(2-((2-((3-fluoro-4-(4-(4-propylpiperazin-1-yl)piperidin-1-yl)phenyl)amino)-7H-pyrrolo[2,3-d]pyrimidine-4-yl)amino)phenyl)-N-methylmethanesulfonamide;

17) N-(2-((2-((3-fluoro-4-(4-(4-cyclopropylpiperazin-1-yl)piperidin-1-yl)phenyl)amino)-7H-pyrrolo[2,3-d]pyrimidine-4-yl)amino)phenyl)-N-methylmethanesulfonamide;

18) N-(2-((2-((3-fluoro-4-(4-morpholinopiperidin-1-yl)phenyl)amino)-7H-pyrrolo[2,3-d]pyrimidine-4-yl)amino)phenyl)-N-methylmethanesulfonamide;

19) N-(2-((2-((3-fluoro-4-(4-(4-(oxetan-3-yl)piperazin-1-yl)piperidin-1-yl)phenyl)amino)-7H-pyrrolo[2,3-d]pyrimidine-4-yl)amino)phenyl)-N-methylmethanesulfonamide;

20) N-(2-((2-((3-fluoro-4-(1-methylpiperidin-4-yl)phenyl)amino)-7H-pyrrolo[2,3-d]pyrimidine-4-yl)amino)phenyl)-N-methylmethanesulfonamide;

21) N-(2-((2-((4-(4-(dimethylamino)piperidin-1-yl)-3-fluorophenyl)amino)-7H-pyrrolo[2,3-d]pyrimidine-4-yl)amino)phenyl)-N-methylmethanesulfonamide;

22) N-(2-((2-((4-(piperidin-1-yl)-3-fluorophenyl)amino)-7H-pyrrolo[2,3-d]pyrimidine-4-yl)amino)phenyl)-N-methylmethanesulfonamide;

23) N-(2-((2-((3-fluoro-4-(piperazin-1-yl)phenyl)amino)-7H-pyrrolo[2,3-d]pyrimidine-4-yl)amino)phenyl)-N-methylmethanesulfonamide;

24) N-(2-((2-((3-fluoro-4-((1-methylpiperidin-4-yl)amino)phenyl)amino)-7H-pyrrolo[2,3-d]pyrimidine-4-yl)amino)phenyl)-N-methylmethanesulfonamide;

25) N-(2-((2-(3,5-difluoro-4-(4-methylpiperazin-1-yl)phenyl)amino)-7H-pyrrolo[2,3-d]pyrimidine-4-yl)amino)phenyl)-N-methylmethanesulfonamide;

26) N-(2-((2-((4-(4-ethylpiperazin-1-yl)-3,5-difluorophenyl)amino)-7H-pyrrolo[2,3-d]pyrimidine-4-yl)amino)phenyl)-N-methylmethanesulfonamide;

27) N-(2-((2-((2,3-difluoro-4-(4-methylpiperazin-1-yl)phenyl)amino)-7H-pyrrolo[2,3-d]pyrimidine-4-yl)amino)phenyl)-N-methylmethanesulfonamide;

28) N-(2-((2-((2,3-difluoro-4-(4-(2-hydroxyethyl)piperazin-1-yl)phenyl)amino)-7H-pyrrolo[2,3-d]pyrimidine-4-yl)amino)phenyl)-N-methylmethanesulfonamide;

29) N-methyl-N-(2-((2-((5-(4-methylpiperazin-1-yl)pyridin-2-yl)amino)-7H-pyrrolo[2,3-d]pyrimidine-4-yl)amino)phenyl)methanesulfonamide;

30) N-methyl-N-(2-((2-((6-(4-methylpiperazin-1-yl)pyridin-3-yl)amino)-7H-pyrrolo[2,3-d]pyrimidine-4-yl)amino)phenyl)methanesulfonamide;

31) N-(2-((2-((3-fluoro-4-(9-methyl-3,9-diazaspiro[5.5]undecan-3-yl)phenyl)amino)-7H-pyrrolo[2,3-d]pyrimidine-4-yl)amino)phenyl)-N-methylmethanesulfonamide;

32) N-(2-((2-((4-(9-ethyl-3,9-diazaspiro[5.5]undecan-3-yl)-3-fluorophenyl)amino)-7H-pyrrolo[2,3-d]pyrimidine-4-yl)amino)phenyl)-N-methanesulfonamide;

33) N-(2-((2-((3-fluoro-4-(2-methyl-2,8-diazaspiro[4.5]decan-8-yl)phenyl)amino)-7H-pyrrolo[2,3-d]pyrimidine-4-yl)amino)phenyl)-N-methylmethanesulfonamide;

34) N-(2-((2-((3-fluoro-4-(2-methyl-2,7-diazaspiro[3.5]nonan-7-yl)phenyl)amino)-7H-pyrrolo[2,3-d]pyrimidine-4-yl)amino)phenyl)-N-methylmethanesulfonamide;

35) N-(2-((2-((3-fluoro-4-(8-methyl-2,8-diazaspiro[4.5]decan-2-yl)phenyl)amino)-7H-pyrrolo[2,3-d]pyrimidine-4-yl)amino)phenyl)-N-methylmethanesulfonamide;

36) N-(2-((2-((3-fluoro-4-(6-methyl-2,6-diazaspiro[3.3]heptan-2-yl)phenyl)amino)-7H-pyrrolo[2,3-d]pyrimidine-4-yl)amino)phenyl)-N-methylmethanesulfonamide;

37) N-(2-((2-((3-fluoro-4-(7-methyl-2,7-diazaspiro[3.5]nonan-2-yl)phenyl)amino)-7H-pyrrolo[2,3-d]pyrimidine-4-yl)amino)phenyl)-N-methylmethanesulfonamide;

38) N-(2-((2-((3-fluoro-4-(6-methyl-2,6-diazaspiro[3.4]octan-2-yl)phenyl)amino)-7H-pyrrolo[2,3-d]pyrimidine-4-yl)amino)phenyl)-N-methylmethanesulfonamide;

39) N-(2-((2-((3-fluoro-4-(3-oxa-9-diazaspiro[5.5]undecan-9-yl)phenyl)amino)-7H-pyrrolo[2,3-d]pyrimidine-4-yl)amino)phenyl)-N-methylmethanesulfonamide;

40) N-(2-((2-((3-fluoro-4-(2-oxa-7-azaspiro[3.5]nonan-7-yl)phenyl)amino)-7H-pyrrolo[2,3-d]pyrimidine-4-yl)amino)phenyl)-N-methylmethanesulfonamide;

41) N-(2-((2-((3-fluoro-4-((3aR,6aS)-5-methylhexahydropyrrolo[3,4-c]pyrrole-2(1H)-yl)phenyl)amino)-7H-pyrrolo[2,3-d]pyrimidine-4-yl)amino)phenyl)-N-methylmethanesulfonamide;

42) N-(2-((2-((3-fluoro-4-(4-methylpiperazin-1-yl)phenyl)amino)-7H-pyrrolo[2,3-d]pyrimidine-4-yl)amino)phenyl)methanesulfonamide;

43) N-ethyl-N-(2-((2-((3-fluoro-4-(4-methylpiperazin-1-yl)phenyl)amino)-7H-pyrrolo[2,3-d]pyrimidine-4-yl)amino)phenyl)methanesulfonamide;

44) N-(2-((2-((3-fluoro-4-(4-methylpiperazin-1-yl)phenyl)amino)-7H-pyrrolo[2,3-d]pyrimidine-4-yl)amino)phenyl)-N-isopropylmethanesulfonamide;

45) N-cyclopropyl-N-(2-((2-((3-fluoro-4-(4-methylpiperazin-1-yl)phenyl)amino)-7H-pyrrolo[2,3-d]pyrimidine-4-yl)amino)phenyl)methanesulfonamide;

46) N-(2-((2-((3-fluoro-4-(4-methylpiperazin-1-yl)phenyl)amino)-7H-pyrrolo[2,3-d]pyrimidine-4-yl)amino)phenyl)-N-methylethanesulfonamide;

47) N-(2-((2-((3-fluoro-4-(4-methylpiperazin-1-yl)phenyl)amino)-7H-pyrrolo[2,3-d]pyrimidine-4-yl)amino)phenyl)-N-methylpropan-2-sulfonamide;

48) N-(2-((2-((3-fluoro-4-(4-methylpiperazin-1-yl)phenyl)amino)-7H-pyrrolo[2,3-d]pyrimidine-4-yl)amino)phenyl)-N-methylcyclopropanesulfonamide;

49) N-(2-((2-((4-(4-ethylpiperazin-1-yl)-3-fluorophenyl)amino)-7H-pyrrolo[2,3-d]pyrimidine-4-yl)amino)phenyl)methanesulfonamide;

50) N-ethyl-N-(2-((2-((4-(4-ethylpiperazin-1-yl)-3-fluorophenyl)amino)-7H-pyrrolo[2,3-d]pyrimidine-4-yl)amino)phenyl)methanesulfonamide;

51) N-(2-((2-((4-(4-ethylpiperazin-1-yl)-3-fluorophenyl)amino)-7H-pyrrolo[2,3-d]pyrimidine-4-yl)amino)phenyl)-N-methylethanesulfonamide;

52) N-ethyl-N-(2-((2-((4-(4-ethylpiperazin-1-yl)-3-fluorophenyl)amino)-7H-pyrrolo[2,3-d]pyrimidine-4-yl)amino)phenypethanesulfonamide;

53) N-(2-((2-((4-(4-(4-ethylpiperazin-1-yl)piperidin-1-yl)-3-fluorophenyl)amino)-7H-pyrrolo[2,3-d]pyrimidine-4-yl)amino)phenyl)methanesulfonamide;

54) N-(2-((2-((4-(4-(4-ethylpiperazin-1-yl)piperidin-1-yl)-3-fluorophenyl)amino)-7H-pyrrolo[2,3-d]pyrimidine-4-yl)amino)phenyl)-N-methylethanesulfonamide;
55) N-ethyl-N-(2-((2-((4-(9-ethyl-3,9-diazaspiro[5.5]undecan-3-yl)-3-fluorophenyl)amino)-7H-pyrrolo[2,3-d]pyrimidine-4-yl)amino)phenyl)methanesulfonamide;
56) N-(2-((2-((4-(2-ethyl-2,8-diazaspiro[4.5]decan-8-yl)-3-fluorophenyl)amino)-7H-pyrrolo[2,3-d]pyrimidine-4-yl)amino)phenyl)-N-methylethanesulfonamide;
57) N-(2-((5-chloro-2-((3-fluoro-4-(4-methylpiperazin-1-yl)phenyl)amino)-7H-pyrrolo[2,3-d]pyrimidine-4-yl)amino)phenyl)-N-methylmethanesulfonamide;
58) N-(2-((5-chloro-2-((2,3-difluoro-4-(4-methylpiperazin-1-yl)phenyl)amino)-7H-pyrrolo[2,3-d]pyrimidine-4-yl)amino)phenyl)-N-methylmethanesulfonamide;
59) N-(2-((5-chloro-2-((6-(4-methylpiperazin-1-yl)pyridin-3-yl)amino)-7H-pyrrolo[2,3-d]pyrimidine-4-yl)amino)phenyl)-N-methylmethanesulfonamide;
60) N-(2-((2-((3-fluoro-4-(4-methylpiperazin-1-yl)phenyl)amino)-5-methyl-7H-pyrrolo[2,3-d]pyrimidine-4-yl)amino)phenyl)-N-methylmethanesulfonamide;
61) N-(2-((5-cyano-2-((3-fluoro-4-(4-methylpiperazin-1-yl)phenyl)amino)-7H-pyrrolo[2,3-d]pyrimidine-4-yl)amino)phenyl)-N-methylmethanesulfonamide;
62) N-(2-((5-fluoro-2-((3-fluoro-4-(4-methylpiperazin-1-yl)phenyl)amino)-7H-pyrrolo[2,3-d]pyrimidine-4-yl)amino)phenyl)-N-methylmethanesulfonamide;
63) N-(2-((2-((4-(4-ethylpiperazin-1-yl)-3-fluorophenyl)amino)-5-fluoro-7H-pyrrolo[2,3-d]pyrimidine-4-yl)amino)phenyl)-N-methylmethanesulfonamide
64) N-(2-((5-fluoro-2-((3-fluoro-4-(4-(4-methylpiperazin-1-yl)piperidin-1-yl)phenyl)amino)-7H-pyrrolo[2,3-d]pyrimidine-4-yl)amino)phenyl)-N-methylmethanesulfonamide;
65) N-(2-((2-((3-fluoro-4-(4-(4-methylpiperazin-1-yl)piperidin-1-yl)phenyl)amino)-7-methyl-7H-pyrrolo[2,3-d]pyrimidine-4-yl)amino)phenyl)-N-methylmethanesulfonamide;
66) N-methyl-N-(2-((2-((1-(1-methylpiperidin-4-yl)-1H-pyrazol-4-yl)amino)-7H-pyrrolo[2,3-d]pyrimidine-4-yl)amino)phenyl)methanesulfonamide; and
67) N-(2-((2-((3-fluoro-4-(4-methylpiperazin-1-yl)phenyl)amino)-9H-purin-6-yl)amino)phenyl)-N-methylmethanesulfonamide, or a solvate or a stereoisomer thereof, or a pharmaceutically acceptable salt thereof.

2. A pharmaceutical composition comprising the compound according to claim 1, a solvate or a stereoisomer thereof, or a pharmaceutically acceptable salt thereof, as an active ingredient.

3. The pharmaceutical composition of claim 2, wherein the pharmaceutical composition is formulated in the form of tablets, pills, powders, capsules, a syrup, an emulsion, or a microemulsion.

* * * * *